US012023156B2

(12) United States Patent
Nawana et al.

(10) Patent No.: US 12,023,156 B2
(45) Date of Patent: Jul. 2, 2024

(54) DERMAL PATCH FOR COLLECTING A PHYSIOLOGICAL SAMPLE

(71) Applicant: Satio, Inc., Boston, MA (US)

(72) Inventors: Namal Nawana, Weston, MA (US); Ziad Tarik Al-Shamsie, San Diego, CA (US)

(73) Assignee: Satio, Inc., Boston, MA (US)

( * ) Notice: Subject to any disclaimer, the term of this patent is extended or adjusted under 35 U.S.C. 154(b) by 0 days.

(21) Appl. No.: 18/090,026

(22) Filed: Dec. 28, 2022

(65) Prior Publication Data

US 2023/0137549 A1 May 4, 2023

Related U.S. Application Data

(63) Continuation-in-part of application No. 17/994,454, filed on Nov. 28, 2022, now Pat. No. 11,877,848, and
(Continued)

(51) Int. Cl.
*A61B 5/15* (2006.01)

(52) U.S. Cl.
CPC .. *A61B 5/150099* (2013.01); *A61B 5/150389* (2013.01); *A61B 5/150969* (2013.01)

(58) Field of Classification Search
CPC ............... B01L 3/5023; B01L 2200/04; B01L 2200/10; B01L 2200/16; B01L 2300/023; B01L 2300/044; A61B 5/15109
(Continued)

(56) References Cited

U.S. PATENT DOCUMENTS

| 5,015,228 A | 5/1991 | Columbus et al. |
| 5,338,308 A | 8/1994 | Wilk |

(Continued)

FOREIGN PATENT DOCUMENTS

| AU | 2006283345 A1 | 3/2007 |
| AU | 2016266112 A1 | 12/2016 |

(Continued)

OTHER PUBLICATIONS

English machine translation of JP-2004024164-A, patents.google.com, 8 pages.
(Continued)

*Primary Examiner* — Phillip A Gray
(74) *Attorney, Agent, or Firm* — Potomac Law Group, PLLC; John J. Penny, Jr.

(57) ABSTRACT

A dermal patch system for collecting a physiological sample includes a cartridge configured to attach to the skin of a subject. The cartridge includes a bottom material layer, a middle material layer, a top material layer, and a sample collection pad. The top layer and the middle layer define a vacuum pin receptacle and the vacuum pin is disposed within the vacuum pin receptacle. The vacuum pin creates a vacuum within the cartridge when moved to a deployed position. The system further includes a lancet with a needle (s). The lancet is configured to move the needle(s) from an undeployed position to a deployed position when engaged with into the cartridge. The needle(s) is configured to draw a physiological sample from the subject when the needle(s) is in the deployed position. The vacuum created by the vacuum pin draws the physiological sample to the sample collection pad.

18 Claims, 30 Drawing Sheets

Related U.S. Application Data a continuation-in-part of application No. 17/991,284, filed on Nov. 21, 2022, and a continuation-in-part of application No. 17/971,142, filed on Oct. 21, 2022, and a continuation-in-part of application No. 17/903,802, filed on Sep. 6, 2022, and a continuation-in-part of application No. 17/500,873, filed on Oct. 13, 2021.

(58) Field of Classification Search
USPC .......................................................... 600/309
See application file for complete search history.

(56) References Cited

U.S. PATENT DOCUMENTS

| | | |
|---|---|---|
| 5,441,490 A | 8/1995 | Svedman |
| 5,527,288 A | 6/1996 | Gross et al. |
| 5,602,037 A | 2/1997 | Ostgaard et al. |
| 5,636,640 A | 6/1997 | Staehlin |
| 5,680,872 A | 10/1997 | Sesekura et al. |
| 5,848,991 A | 12/1998 | Gross et al. |
| 5,997,501 A | 12/1999 | Gross et al. |
| 6,234,980 B1 | 5/2001 | Bell |
| 6,315,985 B1 | 11/2001 | Wu et al. |
| 6,454,140 B1 | 9/2002 | Jinks |
| 6,500,150 B1 | 12/2002 | Gross et al. |
| 6,506,168 B1 | 1/2003 | Fathallah et al. |
| 6,524,284 B1 | 2/2003 | Marshall |
| 6,610,273 B2 | 8/2003 | Wu et al. |
| 6,623,457 B1 | 9/2003 | Rosenberg |
| 6,644,517 B2 | 11/2003 | Thiel et al. |
| 6,689,118 B2 | 2/2004 | Alchas et al. |
| 6,776,776 B2 | 8/2004 | Alchas et al. |
| 6,780,171 B2 | 8/2004 | Gabel et al. |
| 6,796,429 B2 | 9/2004 | Cameron et al. |
| 6,808,506 B2 | 10/2004 | Lastovich et al. |
| 6,893,655 B2 | 5/2005 | Flanigan et al. |
| 6,932,082 B2 | 8/2005 | Stein |
| 6,960,193 B2 | 11/2005 | Rosenberg |
| 6,994,691 B2 | 2/2006 | Ejlersen |
| 7,004,928 B2 | 2/2006 | Aceti et al. |
| 7,083,592 B2 | 8/2006 | Lastovich et al. |
| 7,101,534 B1 | 9/2006 | Schultz et al. |
| 7,156,838 B2 | 1/2007 | Gabel et al. |
| 7,175,642 B2 | 2/2007 | Briggs et al. |
| 7,182,955 B2 | 2/2007 | Hart et al. |
| 7,250,037 B2 | 7/2007 | Shermer et al. |
| 7,252,651 B2 | 8/2007 | Haider et al. |
| 7,282,058 B2 | 10/2007 | Levin et al. |
| 7,308,893 B2 | 12/2007 | Boot |
| 7,435,415 B2 | 10/2008 | Gelber |
| 7,637,891 B2 | 12/2009 | Wall |
| 7,651,475 B2 | 1/2010 | Angel et al. |
| 7,678,079 B2 | 3/2010 | Shermer et al. |
| 7,846,488 B2 | 12/2010 | Johnson et al. |
| 7,905,866 B2 | 3/2011 | Haider et al. |
| 8,048,019 B2 | 11/2011 | Nisato et al. |
| 8,057,842 B2 | 11/2011 | Choi et al. |
| 8,066,680 B2 | 11/2011 | Alchas et al. |
| 8,079,960 B2 | 12/2011 | Briggs et al. |
| 8,104,469 B2 | 1/2012 | Dams |
| 8,108,023 B2 | 1/2012 | Mir et al. |
| 8,157,768 B2 | 4/2012 | Haider et al. |
| 8,206,336 B2 | 6/2012 | Shantha |
| 8,246,582 B2 | 8/2012 | Angel et al. |
| 8,246,893 B2 | 8/2012 | Ferguson et al. |
| 8,252,268 B2 | 8/2012 | Slowey et al. |
| 8,267,889 B2 | 9/2012 | Cantor et al. |
| 8,303,518 B2 | 11/2012 | Aceti et al. |
| D681,195 S | 4/2013 | Skulley et al. |
| 8,409,140 B2 | 4/2013 | Ejlersen et al. |
| 8,414,503 B2 | 4/2013 | Briggs et al. |
| 8,414,959 B2 | 4/2013 | Hye-Ok et al. |
| 8,430,097 B2 | 4/2013 | Jinks et al. |
| 8,459,253 B2 | 6/2013 | Howgill |
| 8,491,500 B2 | 7/2013 | Briggs et al. |
| 8,496,601 B2 | 7/2013 | Briggs et al. |
| D687,550 S | 8/2013 | Moeckly et al. |
| D687,551 S | 8/2013 | Moeckly et al. |
| D687,945 S | 8/2013 | Brewer et al. |
| D687,946 S | 8/2013 | Brewer et al. |
| D687,947 S | 8/2013 | Brewer et al. |
| 8,512,244 B2 | 8/2013 | Jennewine |
| 8,517,019 B2 | 8/2013 | Brewer et al. |
| 8,554,317 B2 | 10/2013 | Duan |
| 8,556,861 B2 | 10/2013 | Tsals |
| 8,561,795 B2 | 10/2013 | Schott |
| D693,921 S | 11/2013 | Burton et al. |
| 8,602,271 B2 | 12/2013 | Winker et al. |
| 8,603,040 B2 | 12/2013 | Haider et al. |
| 8,608,889 B2 | 12/2013 | Sever et al. |
| 8,622,963 B2 | 1/2014 | Iwase et al. |
| 8,696,619 B2 | 4/2014 | Schnall |
| 8,696,637 B2 | 4/2014 | Ross |
| D705,422 S | 5/2014 | Burton et al. |
| 8,715,232 B2 | 5/2014 | Yodfat et al. |
| 8,740,014 B2 | 6/2014 | Purkins et al. |
| 8,741,377 B2 | 6/2014 | Choi et al. |
| 8,784,363 B2 | 7/2014 | Frederickson et al. |
| 8,808,202 B2 | 8/2014 | Brancazio |
| 8,808,786 B2 | 8/2014 | Jinks et al. |
| 8,814,009 B2 | 8/2014 | Hodson et al. |
| 8,814,035 B2 | 8/2014 | Stuart |
| 8,821,412 B2 | 9/2014 | Gonzalez-Zugasti et al. |
| 8,821,446 B2 | 9/2014 | Trautman et al. |
| 8,821,779 B2 | 9/2014 | Ferguson et al. |
| 8,827,971 B2 | 9/2014 | Gonzalez-Zugasti et al. |
| 8,870,821 B2 | 10/2014 | Laufer |
| 8,900,180 B2 | 12/2014 | Wolter et al. |
| 8,900,194 B2 | 12/2014 | Clarke et al. |
| 8,945,071 B2 | 2/2015 | Christensen |
| 8,961,431 B2 | 2/2015 | Roe et al. |
| 9,022,973 B2 | 5/2015 | Sexton et al. |
| 9,033,898 B2 | 5/2015 | Chickering, III et al. |
| 9,041,541 B2 | 5/2015 | Levinson et al. |
| D733,290 S | 6/2015 | Burton et al. |
| 9,067,031 B2 | 6/2015 | Jinks et al. |
| 9,072,664 B2 | 7/2015 | Stein et al. |
| 9,089,661 B2 | 7/2015 | Stuart et al. |
| 9,089,677 B2 | 7/2015 | Soo et al. |
| 9,113,836 B2 | 8/2015 | Bernstein et al. |
| 9,119,578 B2 | 9/2015 | Haghgooie et al. |
| 9,119,945 B2 | 9/2015 | Simons et al. |
| 9,133,024 B2 | 9/2015 | Phan et al. |
| 9,144,651 B2 | 9/2015 | Stuart |
| 9,144,671 B2 | 9/2015 | Cantor et al. |
| 9,173,994 B2 | 11/2015 | Ziaie et al. |
| 9,174,035 B2 | 11/2015 | Ringsred et al. |
| 9,186,097 B2 | 11/2015 | Frey et al. |
| 9,227,021 B2 | 1/2016 | Buss |
| 9,289,763 B2 | 3/2016 | Berthier et al. |
| 9,289,925 B2 | 3/2016 | Ferguson et al. |
| 9,289,968 B2 | 3/2016 | Sever et al. |
| 9,295,417 B2 | 3/2016 | Haghgooie et al. |
| 9,295,987 B2 | 3/2016 | Kelly et al. |
| 9,339,956 B2 | 5/2016 | Rendon |
| 9,380,972 B2 | 7/2016 | Fletcher et al. |
| 9,380,973 B2 | 7/2016 | Fletcher et al. |
| 9,468,404 B2 | 10/2016 | Hayden |
| 9,480,428 B2 | 11/2016 | Colin et al. |
| 9,504,813 B2 | 11/2016 | Buss |
| 9,522,225 B2 | 12/2016 | Chong et al. |
| 9,549,700 B2 | 1/2017 | Fletcher et al. |
| 9,555,187 B2 | 1/2017 | Sonderegger et al. |
| 9,566,393 B2 | 2/2017 | Iwase et al. |
| 9,579,461 B2 | 2/2017 | Sonderegger et al. |
| 9,623,087 B2 | 4/2017 | Zhang et al. |
| 9,642,895 B2 | 5/2017 | Dai et al. |
| 9,643,229 B2 | 5/2017 | Wilson et al. |
| 9,675,675 B2 | 6/2017 | Zhang et al. |
| 9,675,752 B2 | 6/2017 | Christensen |
| 9,682,222 B2 | 6/2017 | Burton et al. |
| 9,693,950 B2 | 7/2017 | Determan et al. |
| 9,694,149 B2 | 7/2017 | Jinks et al. |
| 9,717,850 B2 | 8/2017 | Sonderegger |

(56) References Cited

U.S. PATENT DOCUMENTS

| | | |
|---|---|---|
| 9,724,462 B2 | 8/2017 | Rotem |
| 9,730,624 B2 | 8/2017 | Gonzalez-Zugasti et al. |
| 9,770,578 B2 | 9/2017 | Chowdhury |
| 9,775,551 B2 | 10/2017 | Bernstein et al. |
| 9,782,574 B2 | 10/2017 | Simmers |
| 9,789,249 B2 | 10/2017 | Frederickson et al. |
| 9,789,299 B2 | 10/2017 | Simmers |
| 9,844,631 B2 | 12/2017 | Bureau |
| 9,849,270 B2 | 12/2017 | Stockholm |
| D808,515 S | 1/2018 | Atkin et al. |
| 9,861,580 B2 | 1/2018 | Mueting et al. |
| 9,861,801 B2 | 1/2018 | Baker et al. |
| 9,872,975 B2 | 1/2018 | Burton et al. |
| 9,884,151 B2 | 2/2018 | Sullivan et al. |
| 9,895,520 B2 | 2/2018 | Burton et al. |
| 9,956,170 B2 | 5/2018 | Cantor et al. |
| 9,968,767 B1 | 5/2018 | Hasan et al. |
| 9,987,629 B2 | 6/2018 | Berthier et al. |
| 9,993,189 B2 | 6/2018 | Phan et al. |
| 10,004,887 B2 | 6/2018 | Gross et al. |
| 10,010,676 B2 | 7/2018 | Bureau |
| 10,010,706 B2 | 7/2018 | Gonzalez et al. |
| 10,010,707 B2 | 7/2018 | Colburn et al. |
| 10,016,315 B2 | 7/2018 | Letourneau et al. |
| 10,029,845 B2 | 7/2018 | Jinks |
| 10,035,008 B2 | 7/2018 | Brandwein et al. |
| 10,076,649 B2 | 9/2018 | Gilbert et al. |
| 10,080,843 B2 | 9/2018 | Bureau |
| 10,080,846 B2 | 9/2018 | Sonderegger et al. |
| 10,099,043 B2 | 10/2018 | Berry et al. |
| 10,105,524 B2 | 10/2018 | Meyer et al. |
| 10,111,807 B2 | 10/2018 | Baker et al. |
| D834,704 S | 11/2018 | Atkin et al. |
| 10,154,957 B2 | 12/2018 | Zhang et al. |
| 10,155,334 B2 | 12/2018 | Rendon |
| 10,183,156 B2 | 1/2019 | Ross et al. |
| 10,188,335 B2 | 1/2019 | Haghgooie et al. |
| D840,020 S | 2/2019 | Howgill |
| 10,201,691 B2 | 2/2019 | Berry et al. |
| 10,232,157 B2 | 3/2019 | Berry et al. |
| 10,232,160 B2 | 3/2019 | Baker et al. |
| 10,248,765 B1 | 4/2019 | Holmes et al. |
| 10,265,484 B2 | 4/2019 | Stuart et al. |
| 10,272,214 B2 | 4/2019 | Child et al. |
| 10,300,260 B2 | 5/2019 | Wirtanen et al. |
| 10,307,578 B2 | 6/2019 | Frederickson et al. |
| 10,315,021 B2 | 6/2019 | Frederickson et al. |
| 10,327,990 B2 | 6/2019 | Egeland et al. |
| 10,328,248 B2 | 6/2019 | Baker et al. |
| 10,335,560 B2 | 7/2019 | Stein et al. |
| 10,335,562 B2 | 7/2019 | Jinks et al. |
| 10,335,563 B2 | 7/2019 | Brewer et al. |
| 10,357,610 B2 | 7/2019 | Sonderegger |
| 10,384,047 B2 | 8/2019 | Simmers |
| 10,391,290 B2 | 8/2019 | Burton et al. |
| 10,398,885 B2 | 9/2019 | Frits et al. |
| 10,406,339 B2 | 9/2019 | Simmers |
| 10,410,838 B2 | 9/2019 | Hanson et al. |
| 10,426,390 B2 | 10/2019 | Berthier et al. |
| 10,426,739 B2 | 10/2019 | Knutson |
| 10,478,346 B2 | 11/2019 | Knutson |
| 10,492,716 B2 | 12/2019 | Berthier et al. |
| 10,507,286 B2 | 12/2019 | Egeland et al. |
| 10,518,071 B2 | 12/2019 | Kulkarni |
| D872,853 S | 1/2020 | Stuart et al. |
| 10,525,463 B2 | 1/2020 | Kelly et al. |
| 10,542,922 B2 | 1/2020 | Sia et al. |
| 10,543,310 B2 | 1/2020 | Bernstein et al. |
| 10,549,079 B2 | 2/2020 | Burton et al. |
| 10,568,937 B2 | 2/2020 | Hattersley et al. |
| D878,544 S | 3/2020 | Stuart et al. |
| 10,576,257 B2 | 3/2020 | Berry et al. |
| 10,596,333 B2 | 3/2020 | Howgill |
| 10,598,583 B1 | 3/2020 | Peeters et al. |
| 10,638,963 B2 | 5/2020 | Beyerlein et al. |
| 10,646,703 B2 | 5/2020 | Chowdhury |
| 10,653,349 B2 | 5/2020 | Delamarche et al. |
| 10,695,289 B2 | 6/2020 | Brown et al. |
| 10,695,547 B2 | 6/2020 | Burton et al. |
| 10,716,926 B2 | 7/2020 | Burton et al. |
| 10,729,842 B2 | 8/2020 | Hooven et al. |
| 10,772,550 B2 | 9/2020 | Aceti et al. |
| 10,779,757 B2 | 9/2020 | Berthier et al. |
| 10,799,166 B2 | 10/2020 | Gonzalez-Zugasti et al. |
| 10,835,163 B2 | 11/2020 | Haghgooie et al. |
| 10,881,342 B2 | 1/2021 | Kelly et al. |
| 10,888,259 B2 | 1/2021 | Jordan et al. |
| 10,926,030 B2 | 2/2021 | Lanigan et al. |
| 10,932,710 B2 | 3/2021 | Jordan et al. |
| 10,939,860 B2 | 3/2021 | Levinson et al. |
| 10,940,085 B2 | 3/2021 | Baker et al. |
| 10,953,211 B2 | 3/2021 | Ross et al. |
| 11,020,548 B2 | 6/2021 | Stuart et al. |
| 11,033,212 B2 | 6/2021 | Berthier et al. |
| 11,040,183 B2 | 6/2021 | Baker et al. |
| 11,103,685 B2 | 8/2021 | Gonzalez et al. |
| 11,110,234 B2 | 9/2021 | Richardson et al. |
| 11,116,953 B2 | 9/2021 | Kobayashi et al. |
| 11,147,955 B2 | 10/2021 | Gross et al. |
| 11,177,029 B2 | 11/2021 | Levinson et al. |
| 11,197,625 B1 | 12/2021 | Schleicher et al. |
| 11,202,895 B2 | 12/2021 | Davis et al. |
| 11,207,477 B2 | 12/2021 | Hodson |
| 11,247,033 B2 | 2/2022 | Baker et al. |
| 11,253,179 B2 | 2/2022 | Bernstein et al. |
| 11,266,337 B2 | 3/2022 | Jackson et al. |
| 11,273,272 B2 | 3/2022 | Stuart et al. |
| 11,291,989 B2 | 4/2022 | Morrison |
| 11,298,060 B2 | 4/2022 | Jordan et al. |
| 11,298,478 B2 | 4/2022 | Stuart et al. |
| 11,304,632 B2 | 4/2022 | Mou et al. |
| 11,344,684 B2 | 5/2022 | Richardson et al. |
| 11,395,614 B2 | 7/2022 | Berthier et al. |
| 11,452,474 B1 | 9/2022 | Nawana et al. |
| 11,458,289 B2 | 10/2022 | Moeckly et al. |
| 11,497,712 B2 | 11/2022 | Stein et al. |
| 11,497,866 B2 | 11/2022 | Howgill |
| 11,510,602 B1 | 11/2022 | Nawana et al. |
| 2002/0077584 A1 | 6/2002 | Lin et al. |
| 2002/0193740 A1 | 12/2002 | Alchas et al. |
| 2004/0002121 A1 | 1/2004 | Regan et al. |
| 2004/0010207 A1 | 1/2004 | Flaherty et al. |
| 2004/0059256 A1 | 3/2004 | Perez |
| 2004/0059366 A1 | 3/2004 | Sato et al. |
| 2004/0106904 A1 | 6/2004 | Gonnelli et al. |
| 2004/0162467 A1 | 8/2004 | Cook |
| 2005/0106713 A1 | 5/2005 | Phan et al. |
| 2005/0118388 A1 | 6/2005 | Kingsford |
| 2006/0047243 A1 | 3/2006 | Rosenberg |
| 2006/0068490 A1 | 3/2006 | Tang et al. |
| 2006/0142651 A1 | 6/2006 | Brister et al. |
| 2007/0004989 A1 | 1/2007 | Dhillon |
| 2007/0191696 A1 | 8/2007 | Mischler et al. |
| 2008/0003274 A1 | 1/2008 | Kaiser |
| 2008/0287864 A1 | 11/2008 | Rosenberg |
| 2009/0012472 A1 | 1/2009 | Ahm et al. |
| 2009/0036826 A1 | 2/2009 | Sage, Jr. et al. |
| 2009/0099427 A1 | 4/2009 | Jina et al. |
| 2009/0112125 A1 | 4/2009 | Tamir |
| 2009/0198215 A1 | 8/2009 | Chong et al. |
| 2009/0259176 A1 | 10/2009 | Yairi |
| 2010/0198107 A1 | 8/2010 | Groll et al. |
| 2010/0249560 A1 | 9/2010 | Levinson et al. |
| 2010/0256524 A1 | 10/2010 | Levinson et al. |
| 2010/0269837 A1 | 10/2010 | Levinson et al. |
| 2010/0272652 A1 | 10/2010 | Levinson |
| 2011/0009847 A1 | 1/2011 | Levinson et al. |
| 2011/0060280 A1 | 3/2011 | Caffey et al. |
| 2011/0105872 A1 | 5/2011 | Chickering et al. |
| 2011/0105951 A1 | 5/2011 | Bernstein et al. |
| 2011/0105952 A1 | 5/2011 | Bernstein et al. |
| 2011/0125058 A1 | 5/2011 | Levinson et al. |
| 2011/0144463 A1 | 6/2011 | Pesach et al. |
| 2011/0172508 A1 | 7/2011 | Chickering, III et al. |

(56) References Cited

U.S. PATENT DOCUMENTS

| | | |
|---|---|---|
| 2011/0172510 A1 | 7/2011 | Chickering, III et al. |
| 2011/0198221 A1 | 8/2011 | Angelescu |
| 2011/0213335 A1 | 9/2011 | Burton et al. |
| 2011/0245635 A1 | 10/2011 | Fujiwara et al. |
| 2011/0257497 A1 | 10/2011 | Tamada et al. |
| 2011/0288389 A9 | 11/2011 | Levinson et al. |
| 2012/0016308 A1 | 1/2012 | Schott |
| 2012/0041338 A1 | 2/2012 | Chickering, III et al. |
| 2012/0046203 A1 | 2/2012 | Walsh et al. |
| 2012/0078224 A1 | 3/2012 | Lerner et al. |
| 2012/0109066 A1 | 5/2012 | Chase et al. |
| 2012/0123297 A1 | 5/2012 | Brancazio |
| 2012/0259599 A1 | 10/2012 | Deck et al. |
| 2012/0271123 A1 | 10/2012 | Castle et al. |
| 2012/0271125 A1 | 10/2012 | Bernstein et al. |
| 2012/0275955 A1 | 11/2012 | Haghgooie et al. |
| 2012/0277629 A1 | 11/2012 | Bernstein et al. |
| 2012/0277696 A1 | 11/2012 | Gonzalez-Zugasti et al. |
| 2012/0277697 A1 | 11/2012 | Haghgooie et al. |
| 2013/0018279 A1 | 1/2013 | Plante et al. |
| 2013/0158468 A1 | 6/2013 | Bernstein et al. |
| 2013/0158482 A1 | 6/2013 | Davis et al. |
| 2013/0211289 A1 | 8/2013 | Moga et al. |
| 2013/0253446 A1 | 9/2013 | Duan et al. |
| 2013/0269423 A1 | 10/2013 | Angelescu |
| 2014/0066843 A1 | 3/2014 | Zhang et al. |
| 2014/0109900 A1 | 4/2014 | Jinks |
| 2014/0194854 A1 | 7/2014 | Tsals |
| 2014/0305823 A1 | 10/2014 | Gelfand et al. |
| 2014/0309555 A1 | 10/2014 | Gelfand et al. |
| 2014/0309557 A1 | 10/2014 | Fletcher et al. |
| 2014/0336616 A1 | 11/2014 | Edwards |
| 2015/0057510 A1 | 2/2015 | Levinson et al. |
| 2015/0057901 A1 | 2/2015 | Sundholm et al. |
| 2015/0073385 A1 | 3/2015 | Lyon et al. |
| 2015/0087944 A1 | 3/2015 | Levinson et al. |
| 2015/0136122 A1 | 5/2015 | Stuart et al. |
| 2015/0250959 A1 | 9/2015 | Stuart et al. |
| 2015/0258272 A1 | 9/2015 | Sullivan et al. |
| 2015/0278476 A1 | 10/2015 | Levinson et al. |
| 2015/0352295 A1 | 12/2015 | Burton et al. |
| 2016/0038068 A1 | 2/2016 | Chickering, III et al. |
| 2016/0051981 A1 | 2/2016 | Berthier et al. |
| 2016/0067468 A1 | 3/2016 | Chowdhury |
| 2016/0136365 A1 | 5/2016 | Stuart et al. |
| 2016/0144100 A1 | 5/2016 | Gharib et al. |
| 2016/0199581 A1 | 7/2016 | Cachemaille et al. |
| 2016/0213295 A1 | 7/2016 | Matsunami et al. |
| 2016/0256095 A1 | 9/2016 | Krasnow et al. |
| 2016/0262676 A1 | 9/2016 | Haghgooie et al. |
| 2016/0315123 A1 | 10/2016 | Kim et al. |
| 2016/0324506 A1 | 11/2016 | Tariyal et al. |
| 2016/0354589 A1 | 12/2016 | Kobayashi et al. |
| 2016/0361006 A1 | 12/2016 | Bullington et al. |
| 2017/0001192 A1 | 1/2017 | Kelly et al. |
| 2017/0014822 A1 | 1/2017 | Ker |
| 2017/0021067 A1 | 1/2017 | Todd et al. |
| 2017/0021117 A1 | 1/2017 | Howgill |
| 2017/0035337 A1 | 2/2017 | Wilkinson et al. |
| 2017/0035975 A1 | 2/2017 | Myung et al. |
| 2017/0043103 A1 | 2/2017 | Wotton et al. |
| 2017/0059304 A1 | 3/2017 | Ma et al. |
| 2017/0120022 A1 | 5/2017 | Chickering, III et al. |
| 2017/0122846 A1 | 5/2017 | Holmes et al. |
| 2017/0127991 A1 | 5/2017 | Bernstein et al. |
| 2017/0173288 A1 | 6/2017 | Stam et al. |
| 2017/0197029 A1 | 7/2017 | Cindrich et al. |
| 2017/0224912 A1 | 8/2017 | Yodfat et al. |
| 2017/0231543 A1 | 8/2017 | Cunningham et al. |
| 2017/0290977 A1 | 10/2017 | Schauderna et al. |
| 2018/0001029 A1 | 1/2018 | Egeland et al. |
| 2018/0008183 A1 | 1/2018 | Chickering, III et al. |
| 2018/0008703 A1 | 1/2018 | Johnson |
| 2018/0008808 A1 | 1/2018 | Chowdhury |
| 2018/0021559 A1 | 1/2018 | Xu |
| 2018/0078241 A1 | 3/2018 | Moga et al. |
| 2018/0103884 A1 | 4/2018 | Delamarche et al. |
| 2018/0126058 A1 | 5/2018 | Nakka David et al. |
| 2018/0132515 A1 | 5/2018 | Lawrence et al. |
| 2018/0132774 A1 | 5/2018 | Gonzalez-Zugasti et al. |
| 2018/0242890 A1 | 8/2018 | Chickering, III et al. |
| 2018/0243543 A1 | 8/2018 | Baek et al. |
| 2018/0296148 A1 | 10/2018 | Gelfand et al. |
| 2018/0344631 A1 | 12/2018 | Zhang et al. |
| 2018/0369512 A1 | 12/2018 | Blatchford et al. |
| 2019/0000365 A1* | 1/2019 | Beyerlein ........ A61B 5/150022 |
| 2019/0001076 A1 | 1/2019 | Solomon et al. |
| 2019/0001081 A1 | 1/2019 | Guion et al. |
| 2019/0001085 A1 | 1/2019 | Cottenden et al. |
| 2019/0015584 A1 | 1/2019 | Meehan et al. |
| 2019/0015827 A1 | 1/2019 | Berthier et al. |
| 2019/0022339 A1 | 1/2019 | Richardson et al. |
| 2019/0023473 A1 | 1/2019 | Schott |
| 2019/0030260 A1 | 1/2019 | Wotton et al. |
| 2019/0053740 A1 | 2/2019 | Bernstein et al. |
| 2019/0054010 A1 | 2/2019 | Slowey et al. |
| 2019/0142318 A1 | 5/2019 | Diebold et al. |
| 2019/0159709 A1 | 5/2019 | Barone et al. |
| 2019/0209820 A1 | 7/2019 | Chickering, III et al. |
| 2019/0240470 A1 | 8/2019 | Frederickson et al. |
| 2019/0298943 A1 | 10/2019 | Stuart et al. |
| 2019/0336058 A1 | 11/2019 | Haghgooie et al. |
| 2019/0366067 A1 | 12/2019 | Ginggen et al. |
| 2020/0009364 A1 | 1/2020 | Amir |
| 2020/0010219 A1 | 1/2020 | Felippone et al. |
| 2020/0011860 A1 | 1/2020 | Nawana et al. |
| 2020/0033008 A1 | 1/2020 | Baker |
| 2020/0069897 A1 | 3/2020 | Hodson et al. |
| 2020/0085414 A1 | 3/2020 | Berthier et al. |
| 2020/0101219 A1 | 4/2020 | Wang et al. |
| 2020/0147209 A1 | 5/2020 | Johnson |
| 2020/0163603 A1 | 5/2020 | Jordan et al. |
| 2020/0164359 A1 | 5/2020 | Jordan et al. |
| 2020/0246560 A1 | 8/2020 | Hodson et al. |
| 2020/0253521 A1 | 8/2020 | Ivosevic et al. |
| 2020/0261668 A1 | 8/2020 | Hodson et al. |
| 2020/0289808 A1 | 9/2020 | Moeckly et al. |
| 2020/0297945 A1 | 9/2020 | Cottenden et al. |
| 2020/0353155 A1 | 11/2020 | Bernstein et al. |
| 2021/0022681 A1 | 1/2021 | Chickering, III et al. |
| 2021/0030975 A1 | 2/2021 | Burton et al. |
| 2021/0059588 A1 | 3/2021 | Welch et al. |
| 2021/0100487 A1 | 4/2021 | Cho et al. |
| 2021/0121110 A1 | 4/2021 | Kelly et al. |
| 2021/0170153 A1 | 6/2021 | Ross et al. |
| 2021/0196567 A1 | 7/2021 | Baker et al. |
| 2021/0228124 A1 | 7/2021 | Gonzalez-Zugasti et al. |
| 2021/0259599 A1 | 8/2021 | Haghgooie et al. |
| 2021/0298679 A1 | 9/2021 | Pierart |
| 2021/0330227 A1 | 10/2021 | Levinson et al. |
| 2021/0369150 A1 | 12/2021 | Bernstein et al. |
| 2021/0378567 A1 | 12/2021 | Weidemaier et al. |
| 2022/0031211 A1 | 2/2022 | Yakhnich et al. |
| 2022/0058895 A1 | 2/2022 | Han |
| 2022/0062607 A1 | 3/2022 | Davis et al. |
| 2022/0071534 A9 | 3/2022 | Gonzalez-Zugasti et al. |
| 2022/0133192 A1 | 5/2022 | Brancazio |
| 2022/0134072 A1 | 5/2022 | Kosel et al. |
| 2022/0215921 A1 | 7/2022 | Levinson et al. |
| 2022/0218251 A1 | 7/2022 | Jackson et al. |
| 2022/0233117 A1 | 7/2022 | Lee et al. |
| 2022/0249818 A1 | 8/2022 | Chickering, III et al. |
| 2022/0257158 A1 | 8/2022 | Haghgooie et al. |
| 2022/0287642 A1 | 9/2022 | Chickering, III et al. |
| 2022/0313128 A1 | 10/2022 | Bernstein et al. |
| 2022/0330860 A1 | 10/2022 | Nawana |
| 2022/0361784 A1 | 11/2022 | Jordan et al. |
| 2023/0109881 A1 | 4/2023 | Nawana et al. |

FOREIGN PATENT DOCUMENTS

| | | |
|---|---|---|
| CN | 101296752 A | 10/2008 |
| EP | 0931507 A1 | 7/1999 |
| EP | 1769735 A1 | 4/2007 |

(56) References Cited

FOREIGN PATENT DOCUMENTS

| | | |
|---|---|---|
| EP | 2493537 A2 | 9/2012 |
| EP | 3513833 A1 | 7/2019 |
| EP | 3490453 B1 | 12/2021 |
| EP | 3962363 A1 | 3/2022 |
| ES | 2550668 T3 | 11/2015 |
| ES | 2565805 T3 | 4/2016 |
| GB | 1492500 A | 11/1977 |
| JP | 2004024164 A | 1/2004 |
| KR | 101857300 B1 | 5/2018 |
| NO | 2012028675 A3 | 5/2012 |
| WO | 9311747 A1 | 6/1993 |
| WO | 9929296 A1 | 6/1999 |
| WO | 0078286 A1 | 12/2000 |
| WO | 0210037 A1 | 2/2002 |
| WO | 0226217 A2 | 4/2002 |
| WO | 0232785 A1 | 4/2002 |
| WO | 02083205 A1 | 10/2002 |
| WO | 02083231 A1 | 10/2002 |
| WO | 02083232 A1 | 10/2002 |
| WO | 03002069 A2 | 1/2003 |
| WO | 03030880 A1 | 4/2003 |
| WO | 03035510 A1 | 5/2003 |
| WO | 03066126 A2 | 8/2003 |
| WO | 03084597 A1 | 10/2003 |
| WO | 03086349 A1 | 10/2003 |
| WO | 03086350 A1 | 10/2003 |
| WO | 03089036 A1 | 10/2003 |
| WO | 2004009172 A1 | 1/2004 |
| WO | 2004022133 A2 | 3/2004 |
| WO | 2004022142 A1 | 3/2004 |
| WO | 2004032990 A2 | 4/2004 |
| WO | 2004039429 A2 | 5/2004 |
| WO | 2004062715 A3 | 10/2004 |
| WO | 2004098576 A1 | 11/2004 |
| WO | 2005006535 A1 | 1/2005 |
| WO | 2005026236 A1 | 3/2005 |
| WO | 2005060441 A2 | 7/2005 |
| WO | 2005014078 A3 | 10/2005 |
| WO | 2005084534 | 10/2005 |
| WO | 2005123173 A1 | 12/2005 |
| WO | 2006016364 A2 | 2/2006 |
| WO | 2006055795 A1 | 5/2006 |
| WO | 2006055799 A1 | 5/2006 |
| WO | 2006055802 A1 | 5/2006 |
| WO | 2006055844 A2 | 5/2006 |
| WO | 2006062848 A1 | 6/2006 |
| WO | 2006062974 A2 | 6/2006 |
| WO | 2006108185 A1 | 10/2006 |
| WO | 2006115663 A2 | 11/2006 |
| WO | 2006135696 A2 | 12/2006 |
| WO | 2007002521 A2 | 1/2007 |
| WO | 2007002522 A1 | 1/2007 |
| WO | 2007002523 A2 | 1/2007 |
| WO | 2007023276 A1 | 3/2007 |
| WO | 2007061781 A1 | 5/2007 |
| WO | 2007064486 A1 | 6/2007 |
| WO | 2007103712 A2 | 9/2007 |
| WO | 2006110723 A3 | 11/2007 |
| WO | 2007124411 A1 | 11/2007 |
| WO | 2008014161 A1 | 1/2008 |
| WO | 2007124406 A3 | 2/2008 |
| WO | 2008008845 A3 | 4/2008 |
| WO | 2008049107 A1 | 4/2008 |
| WO | 2008091602 A3 | 9/2008 |
| WO | 2008121459 A1 | 10/2008 |
| WO | 2008149333 A9 | 1/2009 |
| WO | 2009037192 A1 | 3/2009 |
| WO | 2009046173 A3 | 5/2009 |
| WO | 2009061895 A2 | 5/2009 |
| WO | 2009061907 A2 | 5/2009 |
| WO | 2009056981 A3 | 8/2009 |
| WO | 2009126653 A1 | 10/2009 |
| WO | 2009158300 A1 | 12/2009 |
| WO | 2009142852 A3 | 1/2010 |
| WO | 2010049048 A1 | 5/2010 |
| WO | 2010059605 A2 | 5/2010 |
| WO | 2010062908 A1 | 6/2010 |
| WO | 2010071262 A1 | 6/2010 |
| WO | 2010098339 A1 | 9/2010 |
| WO | 2010101621 A1 | 9/2010 |
| WO | 2010101625 A2 | 9/2010 |
| WO | 2010101626 A1 | 9/2010 |
| WO | 2010101620 A3 | 11/2010 |
| WO | 2010129783 A1 | 11/2010 |
| WO | 2010002613 A3 | 12/2010 |
| WO | 2010110916 A3 | 12/2010 |
| WO | 2010151329 A1 | 12/2010 |
| WO | 2010117602 A3 | 3/2011 |
| WO | 2011016615 A3 | 4/2011 |
| WO | 2011053787 A2 | 5/2011 |
| WO | 2011053788 A2 | 5/2011 |
| WO | 2011053796 A2 | 5/2011 |
| WO | 2011063067 A1 | 5/2011 |
| WO | 2011065972 A2 | 6/2011 |
| WO | 2011071788 A1 | 6/2011 |
| WO | 2011075099 A1 | 6/2011 |
| WO | 2011075103 A1 | 6/2011 |
| WO | 2011075104 A1 | 6/2011 |
| WO | 2011075105 A1 | 6/2011 |
| WO | 2011075569 A1 | 6/2011 |
| WO | 2011084316 A2 | 7/2011 |
| WO | 2011088211 A2 | 7/2011 |
| WO | 2011094573 A1 | 8/2011 |
| WO | 2011014514 | 9/2011 |
| WO | 2011088214 A3 | 9/2011 |
| WO | 2011113114 A1 | 9/2011 |
| WO | 2011116388 A1 | 9/2011 |
| WO | 2011084951 A3 | 11/2011 |
| WO | 2011088211 A3 | 12/2011 |
| WO | 2011150144 A2 | 12/2011 |
| WO | 2011163347 A2 | 12/2011 |
| WO | 2012030316 A1 | 3/2012 |
| WO | 2012018486 A3 | 4/2012 |
| WO | 2012045561 A1 | 4/2012 |
| WO | 2012048388 A1 | 4/2012 |
| WO | 2012049155 A1 | 4/2012 |
| WO | 2012054592 A1 | 4/2012 |
| WO | 2012021792 A3 | 5/2012 |
| WO | 2012061556 A1 | 5/2012 |
| WO | 2012089627 A1 | 7/2012 |
| WO | 2012122162 A1 | 9/2012 |
| WO | 2012145665 A2 | 10/2012 |
| WO | 2012117302 A3 | 11/2012 |
| WO | 2012149126 A1 | 11/2012 |
| WO | 2012149143 A1 | 11/2012 |
| WO | 2012154362 | 12/2012 |
| WO | 2012173971 A1 | 12/2012 |
| WO | 2012149134 | 1/2013 |
| WO | 2012149155 A9 | 3/2013 |
| WO | 2013036602 A1 | 3/2013 |
| WO | 2013050701 A1 | 4/2013 |
| WO | 2013055638 A1 | 4/2013 |
| WO | 2013055641 A1 | 4/2013 |
| WO | 2013059409 A1 | 4/2013 |
| WO | 2013082418 A1 | 6/2013 |
| WO | 2013082427 A1 | 6/2013 |
| WO | 2013090353 A1 | 6/2013 |
| WO | 2013096026 A1 | 6/2013 |
| WO | 2013096027 A1 | 6/2013 |
| WO | 2013112877 A1 | 8/2013 |
| WO | 2013120665 A1 | 8/2013 |
| WO | 2013136176 A1 | 9/2013 |
| WO | 2013136185 A3 | 11/2013 |
| WO | 2013165715 A1 | 11/2013 |
| WO | 2013188609 A1 | 12/2013 |
| WO | 2014004462 A1 | 1/2014 |
| WO | 2014018558 A1 | 1/2014 |
| WO | 2014039367 A1 | 3/2014 |
| WO | 2014052263 A1 | 4/2014 |
| WO | 2014058746 A1 | 4/2014 |
| WO | 2014059104 A1 | 4/2014 |
| WO | 2014078545 A1 | 5/2014 |
| WO | 2014081746 A1 | 5/2014 |
| WO | 2014099404 A1 | 6/2014 |

(56) References Cited

FOREIGN PATENT DOCUMENTS

| | | |
|---|---|---|
| WO | 2014105458 A1 | 7/2014 |
| WO | 2014110016 A1 | 7/2014 |
| WO | 2014096001 A3 | 8/2014 |
| WO | 2014132239 A1 | 9/2014 |
| WO | 2014132240 A1 | 9/2014 |
| WO | 2014153447 A2 | 9/2014 |
| WO | 2014160804 A2 | 10/2014 |
| WO | 2014193725 A1 | 12/2014 |
| WO | 2014193727 A1 | 12/2014 |
| WO | 2014193729 A1 | 12/2014 |
| WO | 2014204951 A1 | 12/2014 |
| WO | 2014186263 A3 | 1/2015 |
| WO | 2015006292 A1 | 1/2015 |
| WO | 2015009523 A1 | 1/2015 |
| WO | 2015009530 A1 | 1/2015 |
| WO | 2015009531 A1 | 1/2015 |
| WO | 2015031552 A1 | 3/2015 |
| WO | 2015034709 A1 | 3/2015 |
| WO | 2015038556 A1 | 3/2015 |
| WO | 2015023649 A3 | 4/2015 |
| WO | 2015072924 A1 | 5/2015 |
| WO | 2015116625 A1 | 8/2015 |
| WO | 2015153570 A1 | 10/2015 |
| WO | 2015153624 A1 | 10/2015 |
| WO | 2015168210 A1 | 11/2015 |
| WO | 2015168215 A1 | 11/2015 |
| WO | 2015168217 A1 | 11/2015 |
| WO | 2015179511 A1 | 11/2015 |
| WO | 2016009986 A1 | 1/2016 |
| WO | 2016018892 A1 | 2/2016 |
| WO | 2016081843 A1 | 5/2016 |
| WO | 2016099986 A2 | 6/2016 |
| WO | 2016100708 A1 | 6/2016 |
| WO | 2016109336 A1 | 7/2016 |
| WO | 2016109339 A1 | 7/2016 |
| WO | 2016109342 A1 | 7/2016 |
| WO | 2016118459 A1 | 7/2016 |
| WO | 2016122915 A1 | 8/2016 |
| WO | 2016132368 A1 | 8/2016 |
| WO | 2016137853 A1 | 9/2016 |
| WO | 2016164508 A1 | 10/2016 |
| WO | 2015168219 | 12/2016 |
| WO | 2017044887 A1 | 3/2017 |
| WO | 2017062727 A1 | 4/2017 |
| WO | 2017062922 A1 | 4/2017 |
| WO | 2017075018 A1 | 5/2017 |
| WO | 2017075586 A1 | 5/2017 |
| WO | 2017087355 A1 | 5/2017 |
| WO | 2017087368 A1 | 5/2017 |
| WO | 2017112400 A1 | 6/2017 |
| WO | 2017112451 A1 | 6/2017 |
| WO | 2017112452 A1 | 6/2017 |
| WO | 2017112748 A1 | 6/2017 |
| WO | 2017113011 A1 | 7/2017 |
| WO | 2017139084 A1 | 8/2017 |
| WO | 2017112476 A3 | 9/2017 |
| WO | 2017176693 A1 | 10/2017 |
| WO | 2017176704 A1 | 10/2017 |
| WO | 2017193076 A1 | 11/2017 |
| WO | 2018022535 A1 | 2/2018 |
| WO | 2018048786 A1 | 3/2018 |
| WO | 2018048790 A1 | 3/2018 |
| WO | 2018048795 A1 | 3/2018 |
| WO | 2018048797 A1 | 3/2018 |
| WO | 2018057760 A1 | 3/2018 |
| WO | 2018128976 A1 | 7/2018 |
| WO | 2018132515 A1 | 7/2018 |
| WO | 2018204217 A1 | 11/2018 |
| WO | 2018213244 A1 | 11/2018 |
| WO | 2019067567 A1 | 4/2019 |
| WO | 2019121324 A1 | 6/2019 |
| WO | 2020025823 A1 | 2/2020 |
| WO | 2020102281 A1 | 5/2020 |
| WO | 2020223710 A1 | 11/2020 |
| WO | 2021007344 A1 | 1/2021 |
| WO | 2021041881 A1 | 3/2021 |
| WO | 2021076846 A1 | 4/2021 |
| WO | 2021121638 A1 | 6/2021 |
| WO | 2021198768 A2 | 10/2021 |
| WO | 2021222066 A1 | 11/2021 |
| WO | 2021222805 A1 | 11/2021 |
| WO | 2022064055 A1 | 3/2022 |

OTHER PUBLICATIONS

International Search Report and Written Opinion for PCT/US2022/046384 mailed Jan. 5, 2023.
International Search Report and Written Opinion for PCT/US2022/048913 mailed Feb. 21, 2023.
International Search Report and Written Opinion for PCT/US22/029829 mailed Nov. 23, 2022.
International Preliminary Report of Patentability, PCT/US2022/029829, Nov. 21, 2023.
International Preliminary Report on Patentability for International Application No. PCT/US2022/024607 dated Oct. 12, 2023.
International Search Report and Written Opinion, PCT/US2022/024607, dated Aug. 4, 2022, 17 pages.
Taiwan Office Action, TW111142334, dated Dec. 12, 2023, 3 pages.
Taiwan Office Action, TW111142334, dated May 18, 2023, 29 pages.
Written Opinion for International Application No. PCT/US2022/024607 issued Oct. 12, 2023.
U.S. Appl. No. 17/719,881, filed Apr. 13, 2022, Self-Contained Dermal Patch for Detection of Physiological Analytes.
U.S. Appl. No. 17/412,205, filed Aug. 25, 2021, Dermal Patch System.
U.S. Appl. No. 17/747,544, filed May 18, 2022, Self-Contained Dermal Patch for Blood Analysis.
U.S. Appl. No. 17/412,213, filed Aug. 25, 2021, Dual Lever Dermal Patch System.
U.S. Appl. No. 17/903,802, filed Sep. 6, 2022, Dual Lever Dermal Patch System.
U.S. Appl. No. 17/500,873, filed Oct. 13, 2021, Mono Dose Dermal Patch for Pharmaceutical Delivery.
U.S. Appl. No. 17/521,466, filed Nov. 8, 2021, Dermal Patch for Collecting a Physiological Sample.
U.S. Appl. No. 17/994,454, filed Nov. 28, 2022, Dermal Patch for Collecting a Physiological Sample.
U.S. Appl. No. 18/411,442, filed Jan. 12, 2024, Dermal Patch for Collecting a Physiological Sample.
U.S. Appl. No. 17/971,142, filed Oct. 21, 2022, Dermal Patch for Collecting a Physiological Sample.
U.S. Appl. No. 17/991,284, filed Nov. 21, 2022, Dermal Patch for Collecting a Physiological Sample with Removable Vial.
U.S. Appl. No. 18/090,063, filed Dec. 28, 2022, Dermal Patch with a Diagnostic Test Strip.
U.S. Appl. No. 18/090,107, filed Dec. 28, 2022, Dermal Patch for Delivering a Pharmaceutical.

\* cited by examiner

DERMAL PATCH FOR COLLECTING A PHYSIOLOGICAL SAMPLE

RELATED APPLICATIONS

The present application is a continuation-in-part of U.S. patent application Ser. No. 17/903,802 (entitled Dual Lever Dermal Patch System and filed on Sep. 6, 2022), Ser. No. 17/500,873 (entitled Mono Dose Dermal Patch for Pharmaceutical Delivery and filed on Oct. 13, 2021), Ser. No. 17/994,454 (entitled Dermal Patch for Collecting a Physiological Sample and filed on Nov. 28, 2022), Ser. No. 17/971,142 (entitled Dermal Patch for Collecting a Physiological Sample and filed on Oct. 21, 2022), and Ser. No. 17/991,284 (entitled Dermal Patch for Collecting a Physiological Sample with Removable Vial and filed on Nov. 21, 2022). Each of these applications is herein incorporated by reference in its entirety.

TECHNICAL FIELD

The present teachings are generally directed to dermal patch systems that can be employed to collect a physiological sample from a subject.

BACKGROUND

Biomarkers are increasingly employed for diagnosis of various disease conditions as well as for assessing treatment protocols. In many cases, it is important to monitor the level of a biomarker over time (e.g., to assess the progression of a disease). The temporal monitoring of biomarkers via conventional techniques includes drawing a physiological fluid sample from a subject. These techniques may be cumbersome and painful to the subject. For example, the invasive nature of drawing a blood sample from a subject can cause discomfort and may lead to less cooperation from a subject, especially children, rendering multiple measurements of a target analyte difficult.

Some recently developed devices allow for continuous monitoring of a target analyte (e.g., glucose monitors). Unfortunately, these devices typically suffer from several shortcomings, such as low sensitivity and/or specificity.

SUMMARY

Aspects of the present disclosure address the above-referenced problems and/or others.

A dermal patch system for collecting a physiological sample includes a cartridge configured to attach to the skin of a subject. The cartridge includes a bottom material layer, a middle material layer, a top material layer, and a sample collection pad. The top layer and the middle layer are coupled to one another and define a vacuum pin receptacle and the vacuum pin is disposed within the vacuum pin receptacle. The vacuum pin creates a vacuum within the cartridge when moved form an undeployed position to a deployed position. The system further includes a lancet with a needle or as many as three needles. The lancet is configured to move the needle(s) from an undeployed position to a deployed position when the lancet is pushed into the cartridge. The needle(s) is configured to direct a physiological sample from the subject when the needle(s) is in the deployed position. The vacuum created by the vacuum pin draws the physiological sample to the sample collection pad. In certain embodiments, the lancet is separate from the cartridge. In some embodiments, capillary flow, wicking and gravity assist the vacuum pin in drawing the physiological sample towards the collection pad.

In some embodiments, the lancet is configured to automatically move the needle(s) to the deployed position when pushed into the cartridge to puncture the skin of a subject. In certain embodiments, the lancet is configured to automatically retract the needle(s) into the lancet from the deployed position. In certain embodiments, the cartridge includes a desiccant. In some embodiments, the bottom layer and the middle layer define a sample well configured to retain the drawn physiological sample. In certain embodiments, the sample well is configured to retain about 60 µl of physiological fluid. In some embodiments, the top layer includes a needle aperture and the needle(s) extends through the needle aperture and the sample well to draw the physiological sample. In certain embodiments, the cartridge includes a sample pathway in open communication with the sample well and the sample collection pad. The sample pathway is configured to carry the physiological sample from the sample well to the sample collection pad.

In certain embodiments, the sample collection pad rests upon the top surface of the middle layer. In some embodiments, the sample collection pad is disposed vertically above the sample pathway. In certain embodiments, the sample pathway extends through the bottom layer and the middle layer. In some embodiments, the cartridge further includes a vacuum pathway in open communication with the sample collection pad. Moving the vacuum pin to the deployed position creates the vacuum within the vacuum pathway and the sample pathway. In certain embodiments, the vacuum pathway extends through the bottom layer and the middle layer. In some embodiments, the sample collection pad is a CF12 collection pad or cellulose paper. In certain embodiments, the cartridge further includes a quick response code disposed on the top layer, wherein the quick response code is associated with an electronic medical record. In some embodiments, the cartridge further includes an adhesive seal that covers the sample collection pad and seals the cartridge. In some embodiments, the sample collection pad is a first sample collection pad and the cartridge includes a second sample collection pad and the vacuum draws the physiological sample to the first sample collection pad and the second sample collection pad.

In another aspect, a method for collecting a physiological sample from a subject, includes attaching a cartridge to a subject. The cartridge includes a bottom material layer, a middle material layer, a top material layer, a sample collection pad, and a vacuum pin. The top layer and middle layer define a vacuum pin receptacle. The vacuum pin is disposed within the vacuum pin receptacle. The method further includes pushing a lancet into the cartridge to draw a physiological sample and pulling the vacuum pin to a deployed position to draw the drawn physiological sample to the sample collection pad. In some embodiments, the lancet is separate from the cartridge.

BRIEF DESCRIPTION OF THE DRAWINGS

Aspects of the present disclosure may take form in various components and arrangements of components, and in various steps and arrangements of steps. The drawings are only for illustration purpose of preferred embodiments of the present disclosure and are not to be considered as limiting.

Features of embodiments of the present disclosure will be more readily understood from the following detailed description take in conjunction with the accompanying drawings in which.

DETAILED DESCRIPTION

Figure 1:
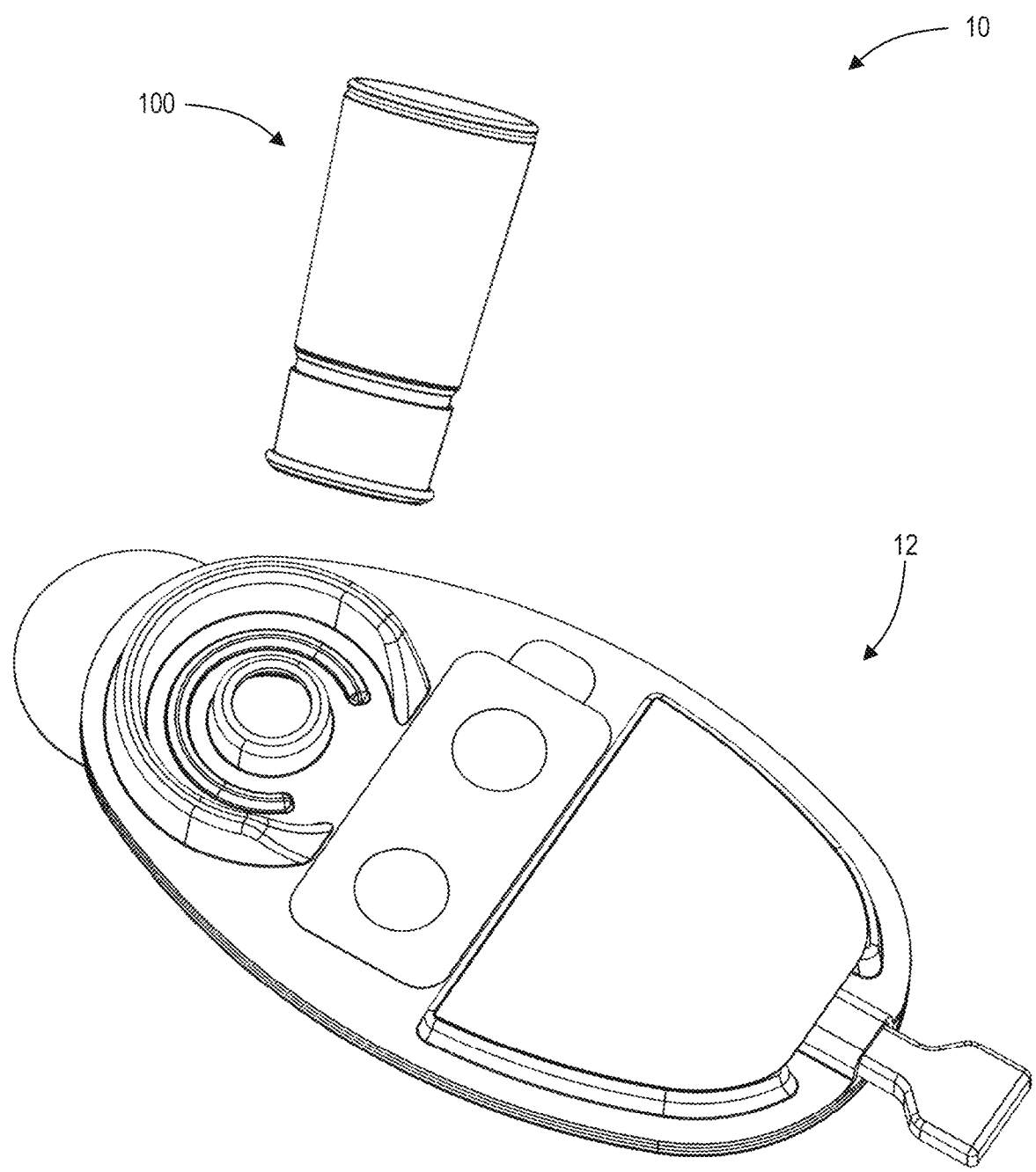
FIG. 1 depicts a dermal patch system in accordance with an exemplary embodiment of the present disclosure.
Figure 2:
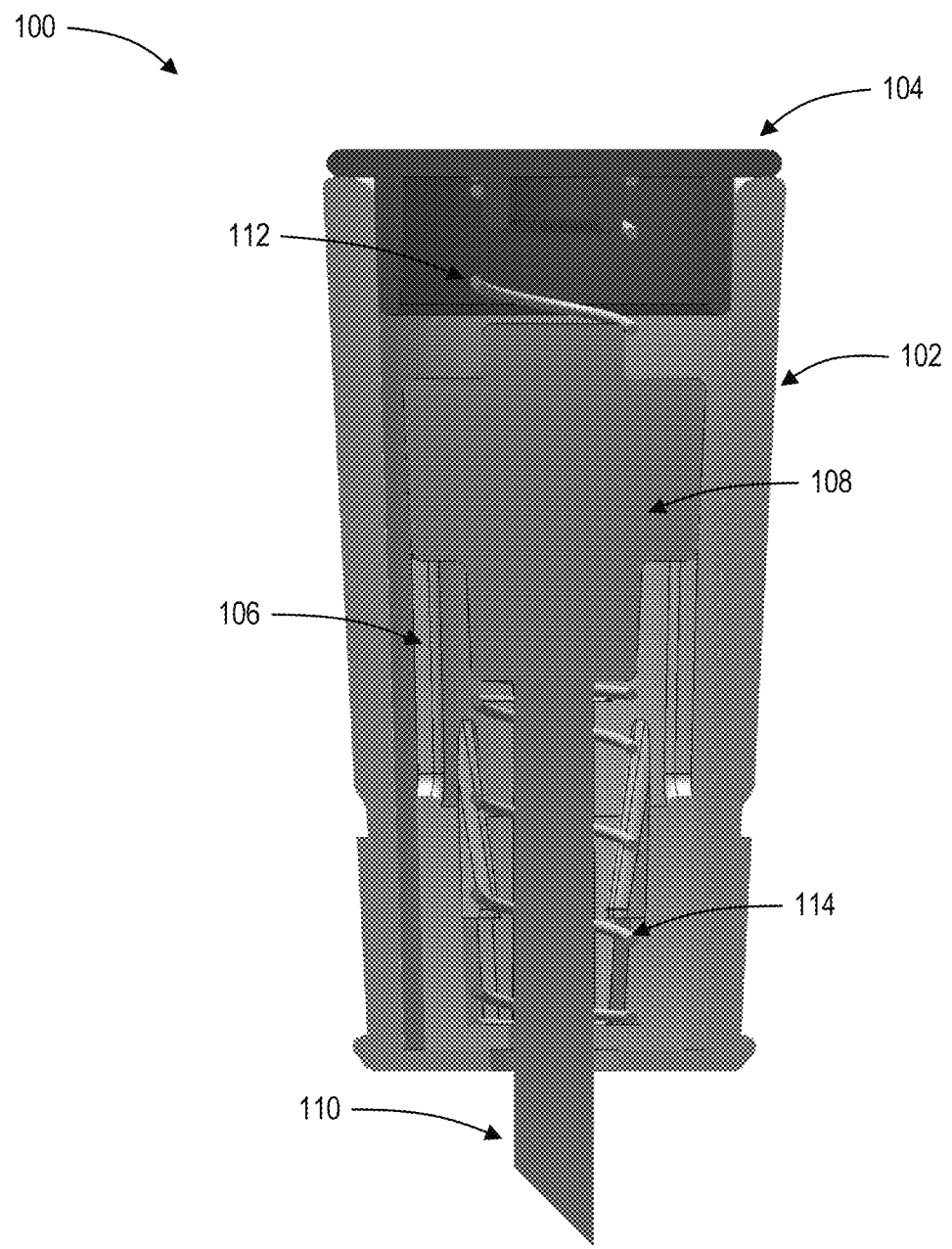
FIG. 2 depicts a lancet of the dermal patch system in accordance with an exemplary embodiment of the present disclosure.

The present disclosure generally relates to a dermal patch system (which may also be referred to as a "dermal patch") that may be utilized to collect and optionally store a physiological sample.

In various embodiments, a dermal patch system may be used to collect a physiological sample and the collected sample may then be stored on a sample collection pad of the dermal patch system. Dermal patch systems disclosed herein may allow for the collection and analysis of a physiological sample in a variety of environments (e.g., at home, in the field, in a medical facility, etc.).

The term "about," as used herein, denotes a deviation of at most 10% relative to a numerical value. For example, about 100 μm means in the range of 90 μm-110 μm.

The term "substantially," as used herein, refers to a deviation, if any, of at most 10% from a complete state and/or condition.

The term "subject" as used herein refers to a human subject or an animal subject (i.e., chicken, pig, cattle, dog, cat, etc.).

The term "transparent," as used herein, indicates that light can substantially pass through an object (e.g., a window) to allow visualization of a material disposed behind the object. For example, in some embodiments, a transparent object allows the passage of at least 70%, or at least 80%, or at least 90% of visible light therethrough.

The term "needle" as used herein, refers to a component with a pointed tip that is configured to pierce an outer surface of an element (e.g., skin of a subject) to provide a passageway through which a physiological fluid can be extracted.

The term "vacuum," as used herein, refers to a pressure less than atmospheric pressure and more particularly to a pressure that can facilitate the movement of a fluid (e.g., a physiological sample) within a dermal patch system according to various embodiments.

The present disclosure generally relates to a device, which is herein also referred to as a dermal patch or a dermal patch system, for collecting a physiological sample (e.g., bodily fluids such as blood, interstitial fluids, etc.) from a subject. In some embodiments discussed below, such a dermal patch system can include a cartridge that can be affixed to a subject's skin (e.g., via an adhesive layer) and a separate lancet that can be engaged with the cartridge to puncture the skin, thereby providing a passageway for extracting the physiological sample. As discussed in more detail below, the lancet can include a housing in which at least one needle that is configured for puncturing the skin is disposed. The lancet can further include a mechanism that can be transitioned between at least two states, wherein in one state (herein referred to as a locked state), the mechanism retains the needle(s) within the lancet in an undeployed position when the lancet is not engaged with the cartridge and in another state (herein referred to as a released state), the mechanism allows the needle(s) to be deployed for puncturing the skin in response to engagement of the lancet with the cartridge. In other words, the engagement of the lancet with the cartridge transitions the mechanism from the locked state to the released state, where in the released state, the mechanism allows the needle(s) to be deployed for puncturing the skin. For example, in some embodiments, the mechanism can include an upper locking portion that can retain an upper spring that is coupled to a needle platform (to which a needle is mounted) in a compressed state, thereby preventing the needle(s) from transitioning into a deployed position. Further, the mechanism can include an upper interference member that prevents the movement of the needle platform when the mechanism is in the locked state.

The engagement of the lancet with the cartridge's housing results in an automatic transition of the mechanism from the locked state to the released state, which transitions the needle(s) into a deployed position in which the needle(s) extends beyond the lancet's housing and the cartridge housing to puncture the subject's skin. In some embodiments, the engagement of the lancet with the cartridge causes the upper locking member to release the needle platform, which in turn allows the upper spring to decompress and thus push down the needle platform thereby deploying the needle(s). In some embodiments, the mechanism can further include a lower interference member that restricts the downward movement of the needle platform, when the needle platform is released. In this manner the extent of the penetration of the needle(s) into the skin can be controlled. In certain embodiments, the mechanism can also include a lower locking member that retains a lower spring in a compressed state. The downward movement of the needle platform can cause the release of the lower locking member to allow the lower spring to decompress and exert a force on the needle platform to cause the retraction of the needle(s) into the lancet housing.

In this manner, the lancet remains safe before it is engaged with the cartridge as the lancet is not capable of deploying the needle(s) when the lancet is not engaged with the cartridge. Furthermore, in this manner, the lancet remains safe after drawing a physiological sample as the needle(s) automatically retracts back into the lancet's housing after being deployed.

Referring now to FIG. 1, a dermal patch system 10 is shown in accordance with an exemplary embodiment. The dermal patch system 10 includes a cartridge 12 that can be affixed to a subject's skin (e.g., via an adhesive layer disposed on a bottom surface of the cartridge 12) and a lancet 100. As will be discussed in further detail herein, the lancet 100 can be activated to deploy a needle disposed within the lancet 100 to puncture the subject's skin thereby drawing a physiological sample from the subject.

Referring to FIGS. 2-6, the lancet 100 is shown in accordance with an exemplary embodiment. The lancet 100 includes a housing 102 in which various components of the lancet are disposed and a cap 104 that is coupled to the housing 102. The lancet 100 can further include an inner sleeve 106 within the housing 102 and a needle frame 108 that is disposed within the inner sleeve 106 and onto which a needle(s) 110 is mounted. While the needle frame 108 is depicted as supporting one needle(s) 110 in other embodiments, the needle frame 108 may support multiple needles 110 (e.g., 2, 3, 4, etc.). The lancet 100 also can include an injection spring 112 and a refraction spring 114 that move a needle of the lancet between various positions.

Figure 3B:
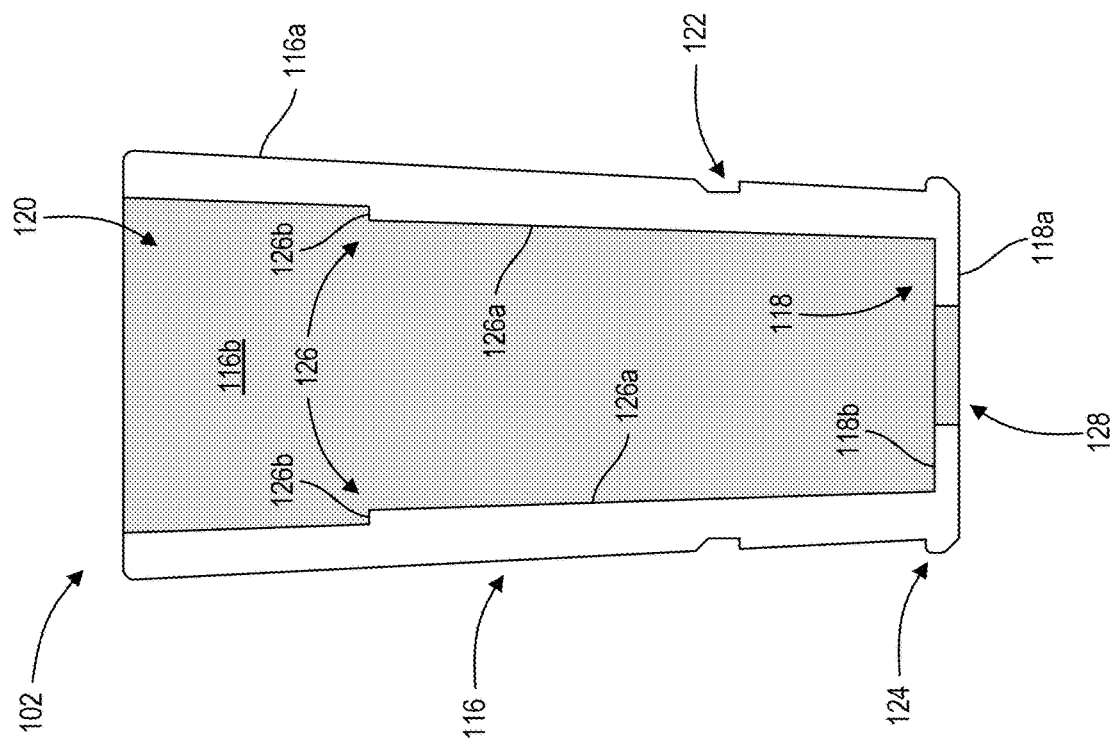
FIGS. 3A and 3B depict a housing of the lancet in accordance with an exemplary embodiment of the present disclosure.
Figure 3A:
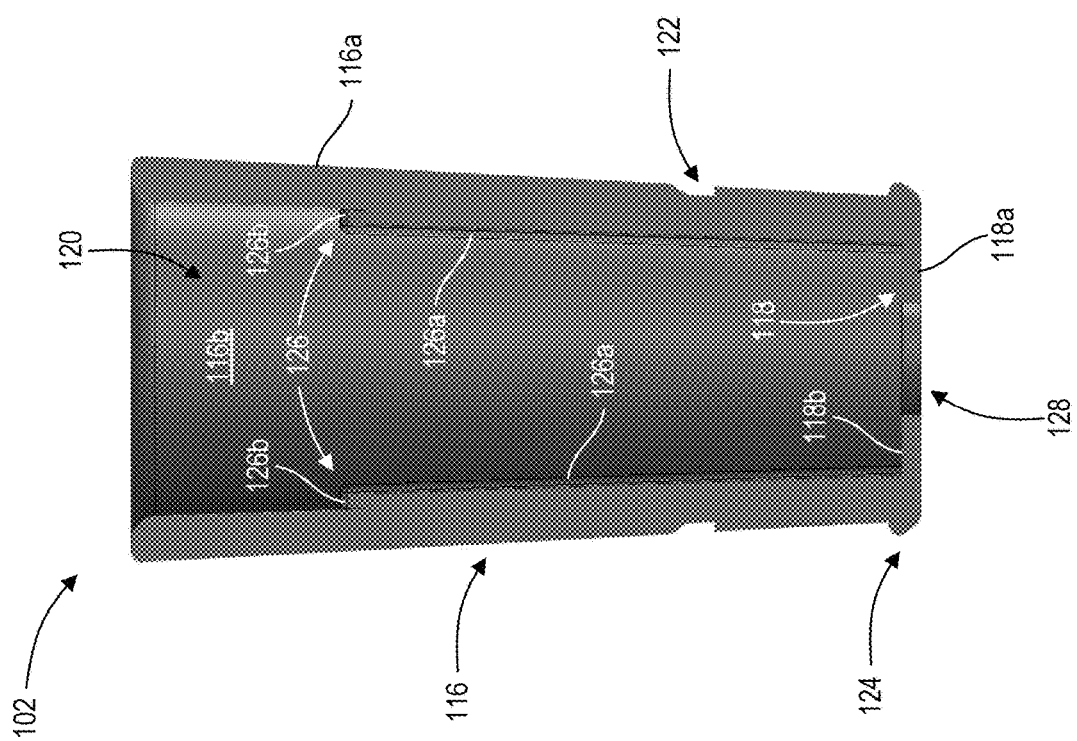

With particular reference to FIGS. 3A and 3B, the housing 102 includes a side wall 116 and a bottom wall 118. The side wall 116 includes an outer surface 116a and an opposed inner surface 116b. The bottom wall 118 includes an outer surface 118a and an opposed inner surface 118b. The side wall 116 extends vertically from the bottom wall 118. The side wall 116 has a generally cylindrical shape and the bottom wall 118 is generally circular in shape and is concentric relative to a longitudinal axis of the generally cylindrical side wall and covers a lower opening formed by the generally cylindrical side wall. The inner surface 116b of the side wall 116 and the inner surface 118b of the bottom wall 118 define an inner volume 120.

The outer surface 116a defines a notch 122 that extends circumferentially around the outer surface 116a of the side wall 116. The housing 102 further includes a rim 124 that extends circumferentially around the outer surface 116a of the side wall 116. The inner surface 116b defines a first and second column 126 that extend vertically from the inner surface 118b of the bottom wall 118. The columns 126 includes an inner surface 126a and a top surface 126b. The inner surface 126a extends vertically between the inner surface 118b of the bottom wall 118 and the top surface 126b. The top surface 126b extends longitudinally between the inner surface 116b of the side wall 116 and the inner surface 126a.

As will be discussed in further detail herein, before the lancet 100 is inserted into the cartridge 12, the columns 126 retain the needle(s) 110 of the lancet 100 in an undeployed position.

The bottom wall 118 defines an aperture 128 that extends through the bottom wall 118. Stated another way, the aperture 128 extends between the outer surface 118a and the inner surface 118b of the bottom wall 118. As will be discussed in further detail herein, when the lancet is activated via engagement with the cartridge 12, the needle(s) of the lancet 100 is activated to extend through the aperture 128 and puncture the subject's skin thereby providing a passageway through which a physiological sample can be drawn from a subject.

Figure 4A:
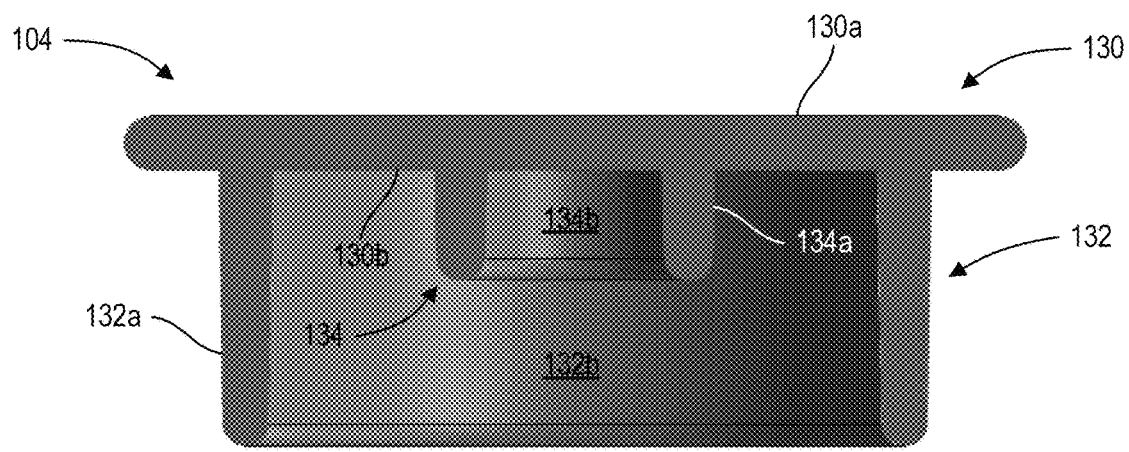
FIGS. 4A and 4B depict a cap of the lancet in accordance with an exemplary embodiment of the present disclosure.
Figure 4B:
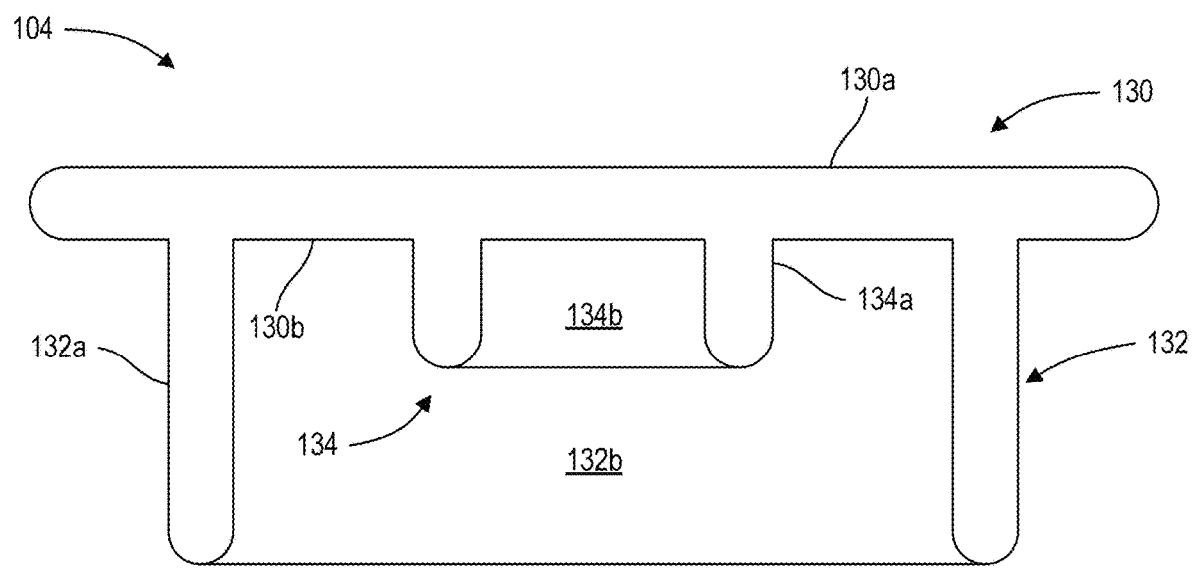

With particular reference to FIGS. 4A and 4B the cap 104 includes a top wall 130 with an outer surface 130a and an opposed inner surface 130b. The cap 104 also includes a side wall 132 with an outer surface 132a and an opposed inner surface 132b. The top wall 130 extends longitudinally from and perpendicular to the side wall 132. The side wall 132 extends vertically from and perpendicular to the top wall 130. The top wall 130 and the side wall 132 are generally circular in shape and are concentric with one another. The cap 104 also includes an inner cylinder 134 with an outer surface 134a and an opposed outer surface 134b. The inner cylinder 134 extends vertically from and perpendicular to the top wall 130. The inner cylinder 134 is concentric with the top wall 130 and the side wall 132.

When the cap 104 is coupled to the housing 102 the side wall 132 extends into the inner volume 120 of the housing 102 and at least a portion of the side wall 132 contacts the inner surface 116b of the side wall 116 such that the cap 104 couples to the housing 102 via an interference fit.

Figure 5:
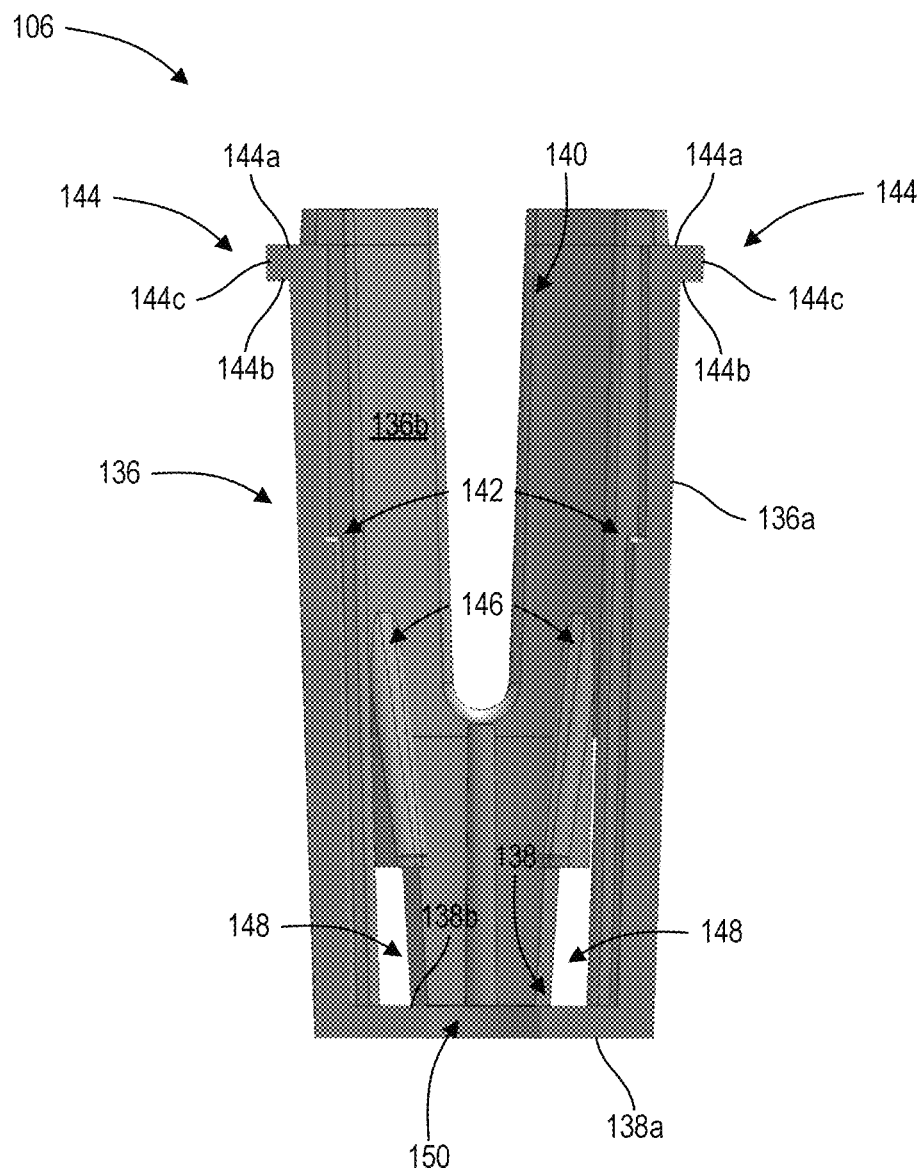
FIG. 5 depicts an inner sleeve of the lancet in accordance with an exemplary embodiment of the present disclosure.

As depicted in FIG. 5, the inner sleeve 106 includes a side wall 136 and a bottom wall 138. The side wall 136 includes an outer surface 136a and an opposed inner surface 136b. The bottom wall 138 includes an outer surface 138a and an opposed inner surface 138b. The side wall 136 extends vertically from the bottom wall 138. The side wall 136 and the bottom wall 138 are generally circular in shape and are concentric with one another. The inner surface 136b of the side wall 136 and the inner surface 138b of the bottom wall 138 define an inner volume 140. The inner surface 136b defines a plurality of columns 142 each of which extends vertically from and perpendicular to the inner surface 138b of the bottom wall 138. As will be discussed in further detail herein, when the needle frame 108 is in a deployed position, a portion of the needle frame 108 rests upon the columns 142.

The inner sleeve 106 further includes a plurality of ledges 144 that extend circumferentially about the side wall 136. Each ledge 144 includes a top surface 144a, an opposed bottom surface 144b and an outer surface 144c that extends between the top surface 144a and the bottom surface 144b. The inner sleeve 106 also includes a plurality of locking members 146 that extend from the inner surface 136b of the side wall 136. As will be discussed in further detail herein, the proximal end of the locking members 146 retains the retraction spring 114 in a compressed state in absence of engagement between the lancet 100 and the cartridge 12. The side wall 136 further defines a plurality of openings 148 that extend through the side wall 136. Stated another way, the openings 148 extend between the outer surface 136a and the inner surface 136b of the side wall 136. Each of the openings 148 is aligned with a proximal end of a locking member 146 to allow the proximal end of a locking member 146 to extend therethrough.

The bottom wall 138 defines an aperture 150 that extends through the bottom wall 138. Stated another way, the aperture 150 extends between the outer surface 138a and the inner surface 138b of the bottom wall 138. The aperture 150 is concentric with the aperture 128 of the housing 102. As will be discussed in further detail herein, when in a deployed position, the needle(s) 110 of the lancet 100 extends through the aperture 150 of the inner sleeve 106 as well as the aperture 128 of the housing 102.

Figure 6:
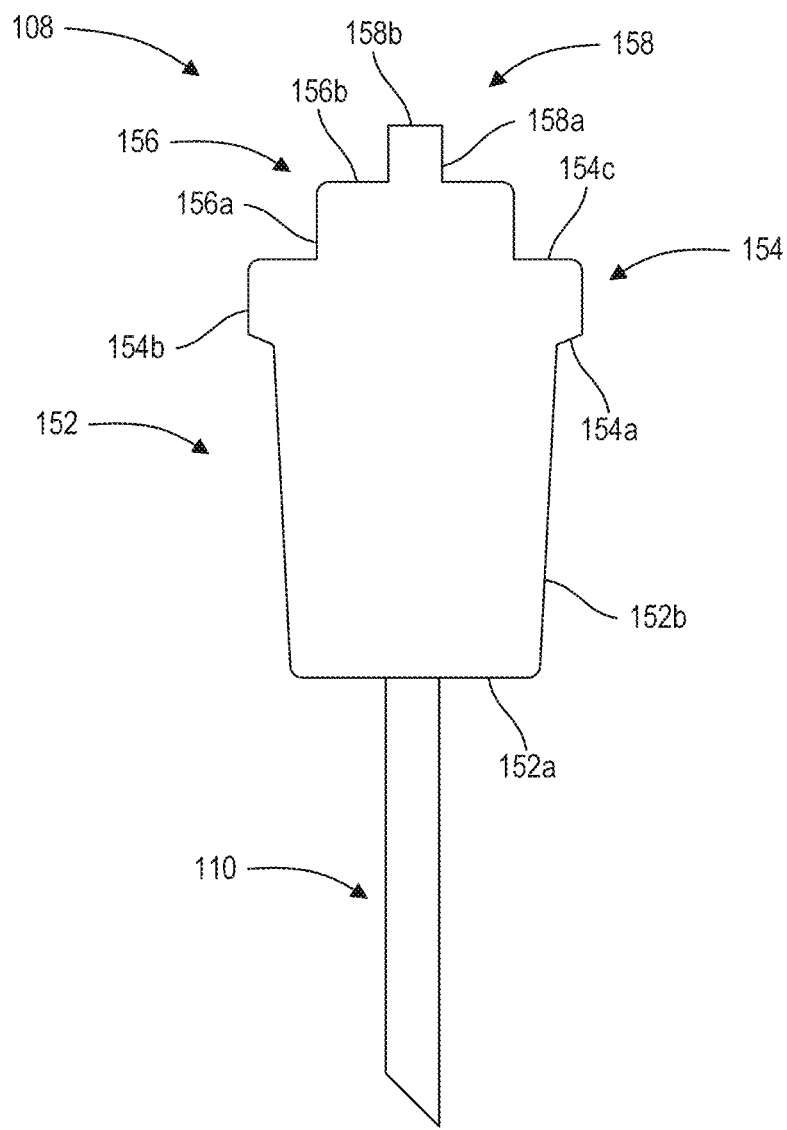
FIG. 6 depicts a needle frame of the lancet in accordance with an exemplary embodiment of the present disclosure.

As depicted in FIG. 6, the needle frame 108 includes a first cylinder 152 and a second cylinder 154 disposed vertically above the second cylinder 154. The first cylinder 152 includes a bottom surface 152a and an outer surface 152b. The second cylinder 154 is disposed vertically above the first cylinder 152 and the third cylinder 156 is disposed vertically above the second cylinder 154. The first cylinder 152 includes a bottom surface 152a and an outer surface 152b and the second cylinder 154 includes a bottom surface 154a, an outer surface 154b and a top surface 154c. The third cylinder 156 includes an outer surface 156a and a top surface 156b. Similarly, the protrusion 158 includes an outer surface 158a and a top surface 158b.

The bottom surface 152a of the first cylinder 152 extends circumferentially about the outer surface 152b of the first cylinder. The outer surface 152b of the first cylinder 152 extends vertically between the bottom surface 152a of the first cylinder 152 and the bottom surface 154a of the second cylinder 154. The bottom surface 154a of the second cylinder 154 extends at an angle longitudinally between the outer surface 152b of the first cylinder and the outer surface 154b of the second cylinder 154. The outer surface 154b extends vertically between the bottom surface 154a and the top surface 154c of the second cylinder 154. The top surface 154c of the second cylinder 154 extends longitudinally between the outer surface 154b of the second cylinder and the outer surface 156a of the third cylinder 156. The outer surface 156a extends vertically between the top surface 154c of the second cylinder and the top surface 156b of the third cylinder. The top surface 156b of the third cylinder extends longitudinally between the outer surface 156a of the third cylinder 156 and the outer surface 158a of the protrusion 158. The outer surface 158a extends vertically between the top surface 156b of the third cylinder and the top surface 158b of the protrusion 158. The top surface 158b of the protrusion 158 extends across a proximal end of the outer surface 158a.

The injection spring 112 extends vertically between the cap 104 and the needle frame 108. More specifically, a distal end of the injection spring 112 contacts the inner surface 130b of the top wall 130 and a proximal end of the injection spring 112 contacts the top surface 154c of the second cylinder 154. The distal end of the injection spring 112 extends circumferentially around the outer surface 134a of the inner cylinder 134. The proximal end of the injection spring 112 extends circumferentially around the third cylinder 156 and around the protrusion 158.

The needle frame 108 supports the needle(s) 110. In some embodiments, the needle(S) 110 is molded into the first cylinder 152 or is attached to the bottom surface 152a of the first cylinder 152 (e.g., via an adhesive).

Figure 7:
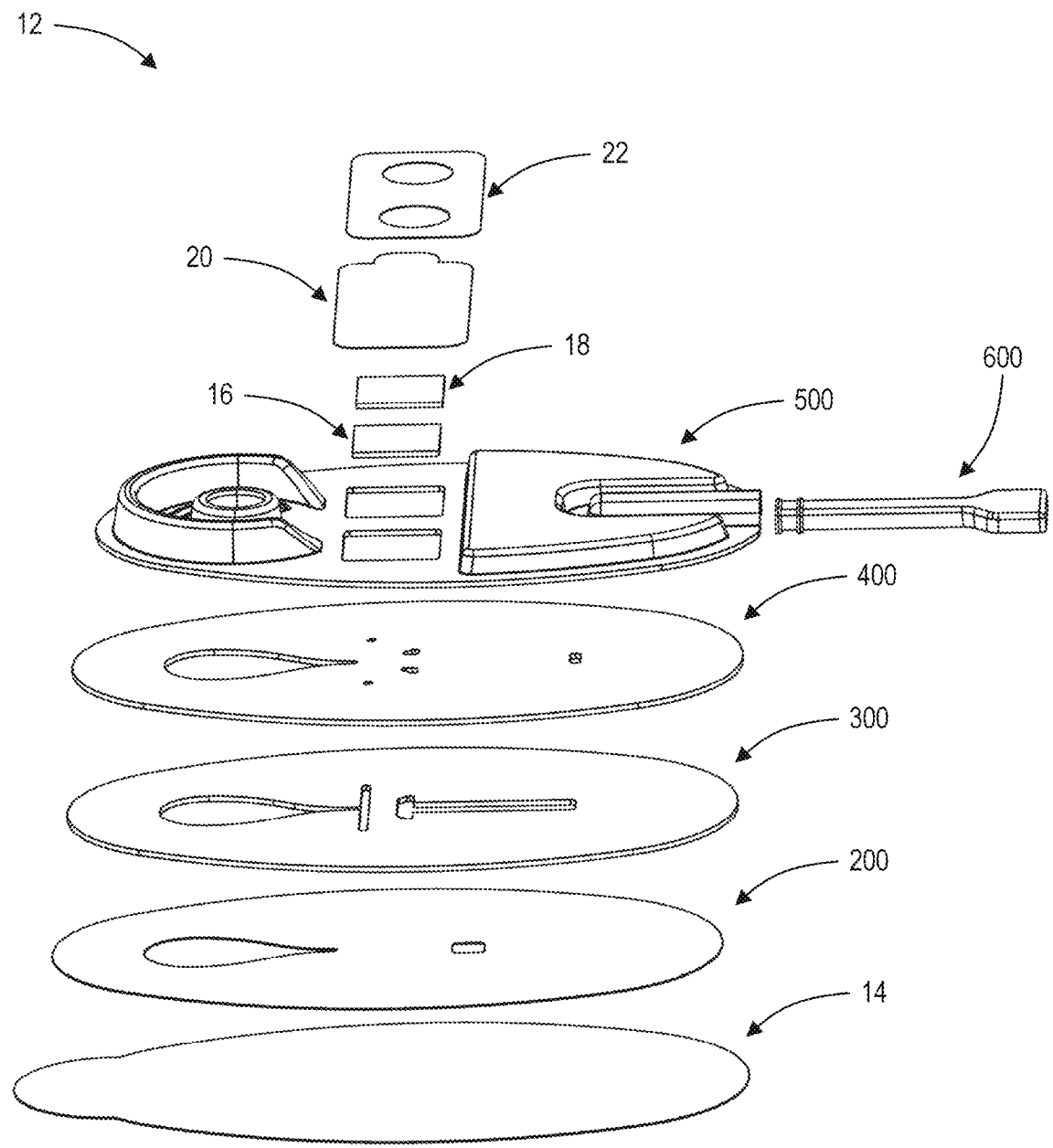
FIG. 7 is an exploded view of a cartridge of the dermal patch system in accordance with an exemplary embodiment of the present disclosure.

Referring to FIG. 7, the cartridge 12 is shown in accordance with an exemplary embodiment. As will be discussed in further detail herein, the cartridge 12 is formed of a plurality of layers of suitable materials including, but not limited to, polymeric materials (e.g., polyolefins, polyethylene terephthalate (PET), polyurethanes, polynorbornenes, polyethers, polyacrylates, polyamides (Polyether block amide also referred to as Pebax®), polysiloxanes, polyether amides, polyether esters, trans-polyisoprenes, polymethyl methacrylates (PMMA), cross-linked trans-polyoctylenes, cross-linked polyethylenes, cross-linked polyisoprenes, cross-linked polycyclooctenes, inorganic-organic hybrid polymers, co-polymer blends with polyethylene and Kraton®, styrene-butadiene co-polymers, urethane-butadiene co-polymers, polycaprolactone or oligo caprolactone co-polymers, polylactic acid (PLLA) or polylactide (PL/DLA) co-polymers, PLLA-polyglycolic acid (PGA) co-polymers, photocross linkable polymers, etc.). In some embodiments, all or a portion of each material layer may be formed of poly(dimethylsiloxane) (PDMS) to allow visibility of components disposed within the cartridge 12. While the various layers of material that form the cartridge 12 are said to be layers of polymeric material, it is understood that the layers of material that form the cartridge 12 may be formed of any suitable material (e.g., metal, metal alloy, etc.). As will be discussed in further detail herein, the layers can be stacked and coupled to one another to form the cartridge 12. In some embodiments, the layers of the cartridge 12 may be formed of aluminum or other suitable metals. In certain embodiments, the layers of the cartridge 12 may be formed of a polymeric coated with aluminum film or another suitable metal film.

The cartridge 12 includes an adhesive layer 200, a bottom layer 300 of polymeric material, a middle layer 400 of polymeric material, a top layer 500 of polymeric material, and a moveable vacuum pin 600 that is disposed between the middle layer 400 and the top layer 500. The cartridge 12 also includes a protective liner 14 (e.g., formed of paper) that covers the adhesive layer 200. The protective liner 14 protects the adhesive layer 200 before the cartridge 12 is attached to the skin of a subject.

Figure 8:
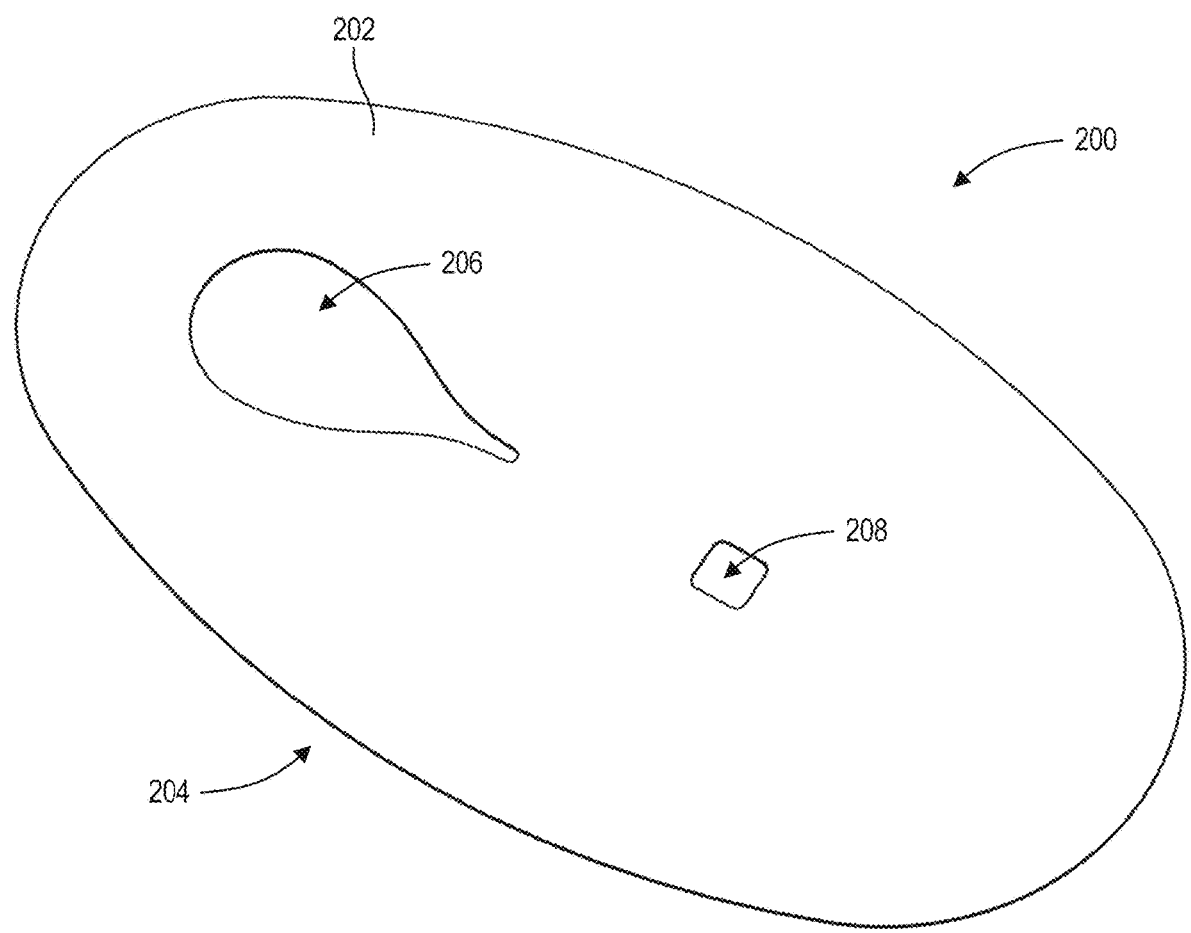
FIG. 8 depicts an adhesive layer of the cartridge in accordance with an exemplary embodiment of the present disclosure.

As depicted in FIG. 8, the adhesive layer 200 includes a top surface 202 and an opposed bottom surface 204. The adhesive layer 200 also includes a sample well opening 206 and an air pathway 208 each of which extends through the adhesive layer 200. That is, the sample well opening 206 and the air pathway 208 extend between the top surface 202 and the bottom surface 204.

Figure 9:
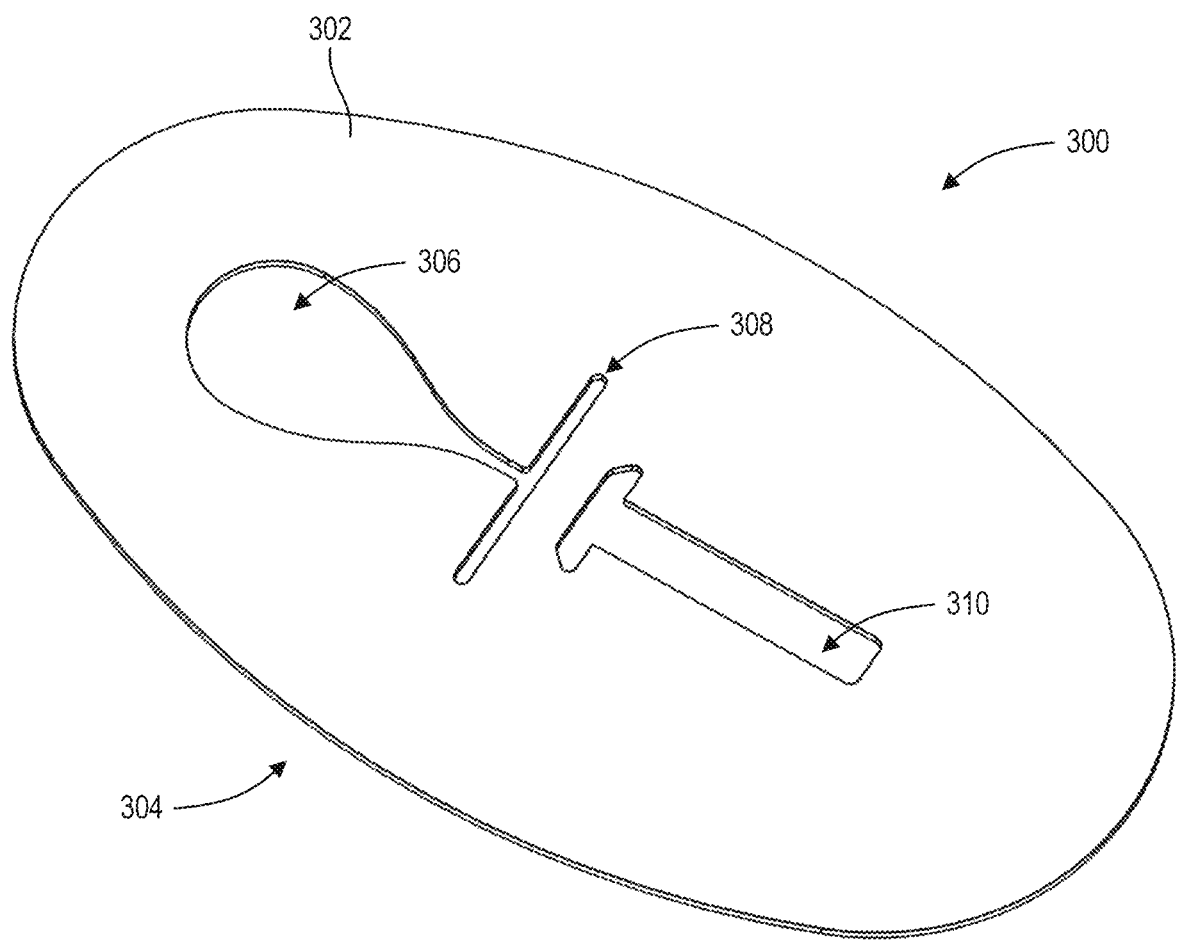
FIG. 9 depicts a bottom layer of the cartridge in accordance with an exemplary embodiment of the present disclosure.

The bottom layer 300 (FIG. 9) can have a thickness in a range of about 0.4 mm to about 0.6 mm (e.g., 0.5 mm) and includes a top surface 302 and an opposed bottom surface 304. The bottom layer 300 also includes a first sample well opening 306 that is connected to a sample channel 308. The bottom layer 300 further includes a T-shaped vacuum channel 310 that is separate from the first sample well opening 306 and the sample channel 308. The first sample well opening 306, the sample channel 308, and the vacuum channel 310 extend through the bottom layer 300. That is, the first sample well opening 306, the sample channel 308, and the vacuum channel 310 extend between the top surface 302 and the bottom surface 304 of the bottom layer 300.

Figure 10:
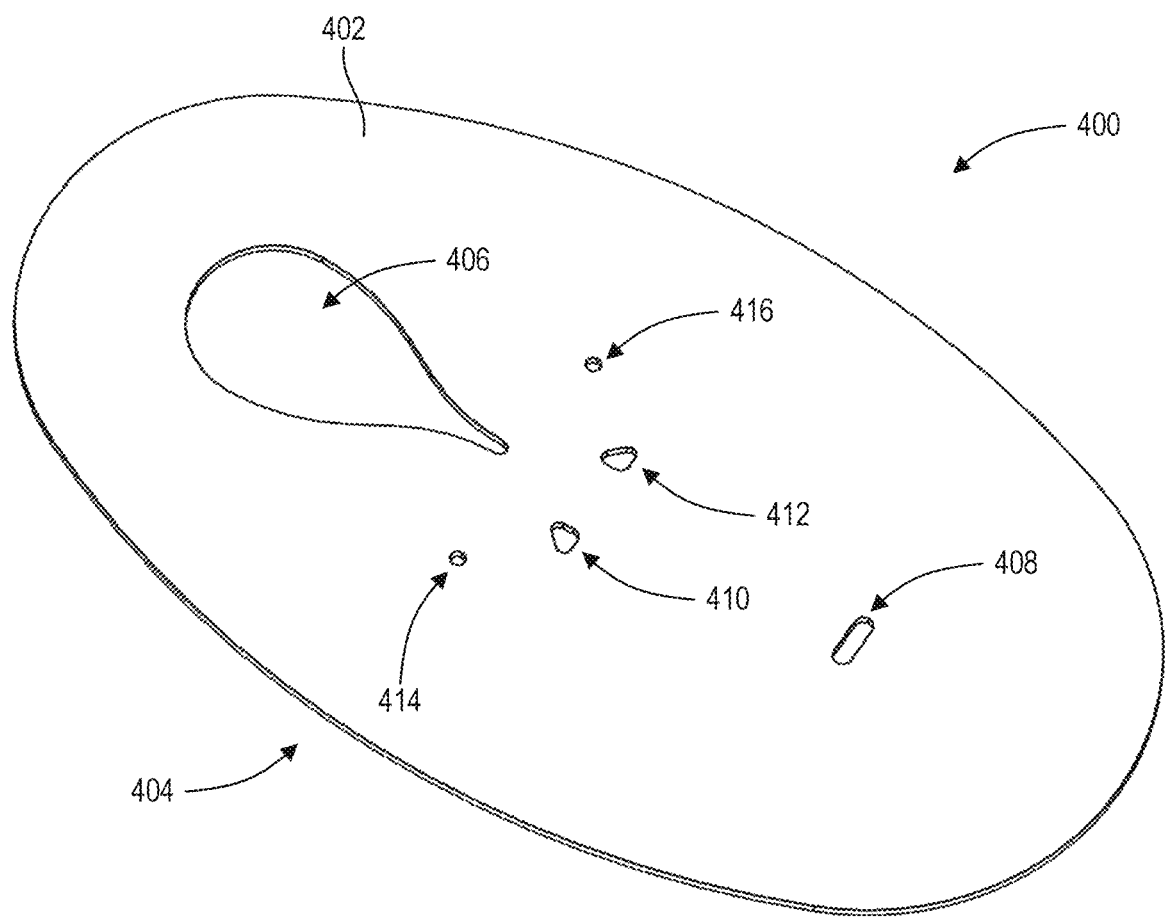
FIG. 10 depicts a middle layer of the cartridge in accordance with an exemplary embodiment of the present disclosure.

By way of example, the middle layer 400 (FIG. 10) can have a thickness in a range of about 0.4 mm to about 0.6 mm (e.g., 0.5 mm) and includes a top surface 402 and an opposed bottom surface 404. The middle layer further includes a sample well opening 406 that is substantially similar in shape and dimension to the first sample well opening 306 of the bottom layer 300. The middle layer 400 also includes a vacuum aperture 408, a first vacuum via 410 and a second vacuum via 412. The first vacuum via 410 and the second vacuum via 412 are substantially similar in shape and dimension. Furthermore, the middle layer 400 includes a first sample via 414 and a second sample via 416 that are substantially similar in shape and dimension. The sample well opening 406, the vacuum aperture 408, the first vacuum via 410, the second vacuum via 412, the first sample via 414, and the second sample via 416 extend through the middle layer 400. That is, the sample well opening 406, the vacuum aperture 408, the first vacuum via 410, the second vacuum via 412, the first sample via 414, and the second sample via 416 extend between the top surface 402 and the bottom surface 404 of the middle layer 400. The sample via 414 and the second sample via 416 may be positioned elsewhere on the middle layer 400 (e.g., closer to a center of the middle layer 400).

Figure 11:
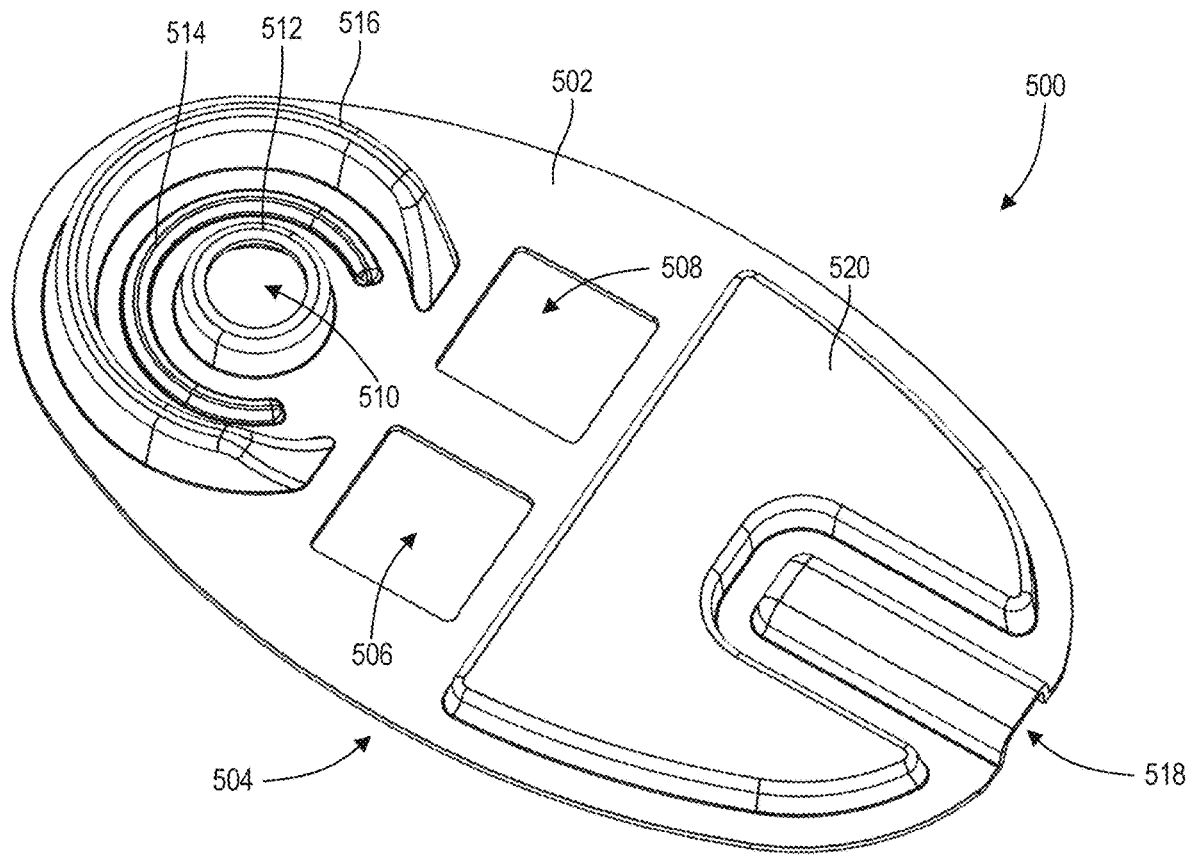
FIGS. 11 and 12 depict a top layer of the cartridge in accordance with an exemplary embodiment of the present disclosure.

By way of example, the top layer 500 (FIGS. 11 and 12) can have a thickness in a range of about 0.4 mm to about 0.7 mm (e.g., 0.45 mm, 0.5 mm, 0.55 mm, 0.6 mm, 0.65 mm, etc.) and includes a top surface 502 and an opposed bottom surface 504. The top layer 500 includes a first sample collection pad opening 506 and a second sample collection pad opening 508 that are substantially similar in shape and dimension. The top layer 500 also includes a circular needle aperture 510. The first sample collection pad opening 506, the second sample collection pad opening 508, and the needle aperture 510 extend through the top layer 500. That is, the first sample collection pad opening 506, the second sample collection pad opening 508, and the needle aperture 510 extend between the top surface 502 and the bottom surface 504 of the top layer 500. The top layer 500 further includes a circular extension 512 that extends vertically from and perpendicular to the top surface 502. The circular extension 512 is concentric with and extends around the needle aperture 510. The top layer 500 also includes a first C-shaped extension 514 and a second C-shaped extension 516 both of which extend vertically from and perpendicular to the top surface 502. The first C-shaped extension 514 and the second C-shaped extension 516 are concentric with and extend partially around the circular extension 512. Furthermore, the top layer 500 defines a groove 518 and includes a raised surface 520. As will be discussed in further detail herein, the groove 518 aids in retaining the vacuum pin 600 within the cartridge 12.

Figure 13:
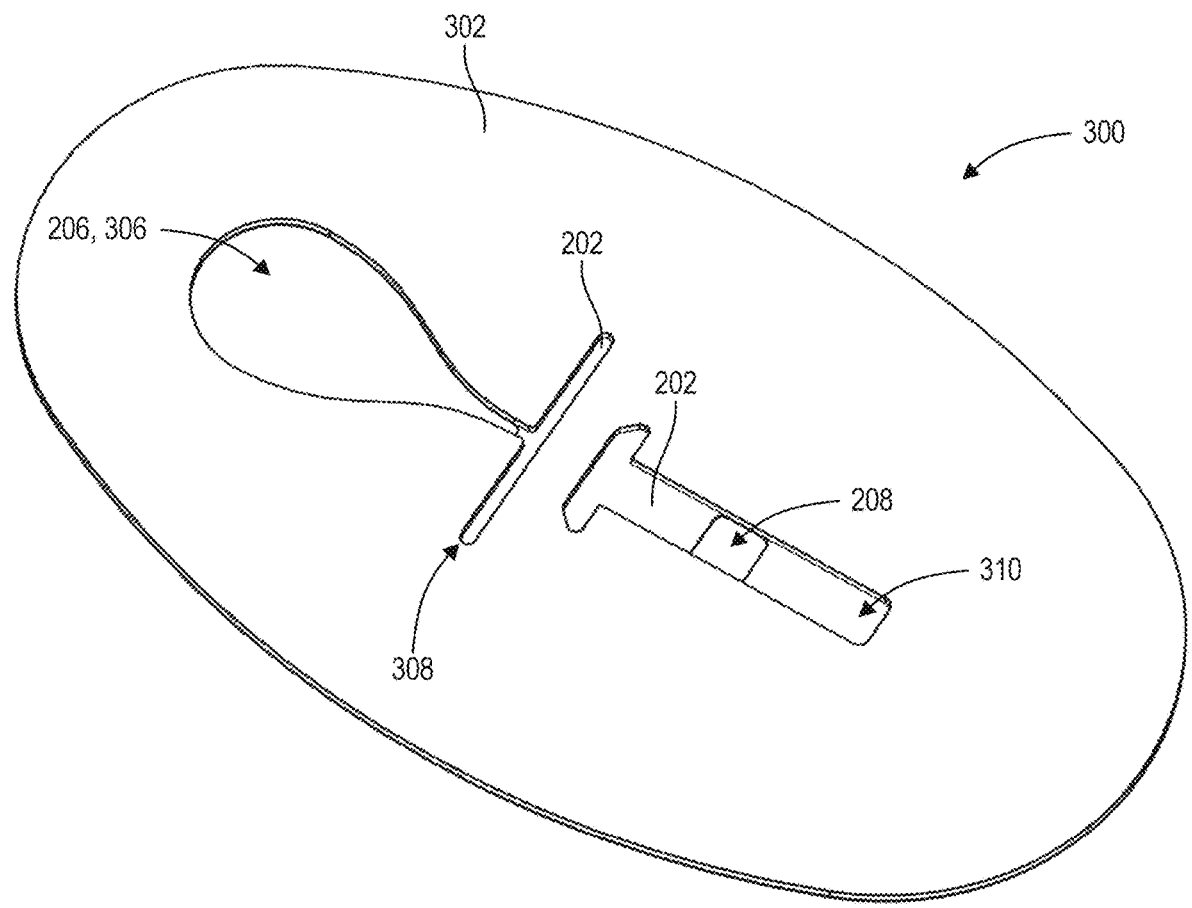
FIG. 13 depicts the adhesive layer and the bottom layer of the cartridge in accordance with an exemplary embodiment of the present disclosure.

With reference to FIG. 13, when the cartridge 12 is assembled, the top surface 202 of the adhesive layer 200 is attached to the bottom surface 304 of the bottom layer 300 such that the sample well opening 206 of the adhesive layer 200 aligns with the sample well opening 306 of the bottom layer 300. Furthermore, when the adhesive layer 200 is attached to the bottom layer 300, the adhesive layer 200 covers the sample channel 308 and covers a majority of the vacuum channel 310. The air pathway 208 aligns with a portion of the vacuum channel 310 to provide an air passageway through the adhesive layer 200 and the bottom layer 300. The air pathway 208 provides airflow and supports the drying of the collection pads before and after collecting the physiological sample.

Figure 14:
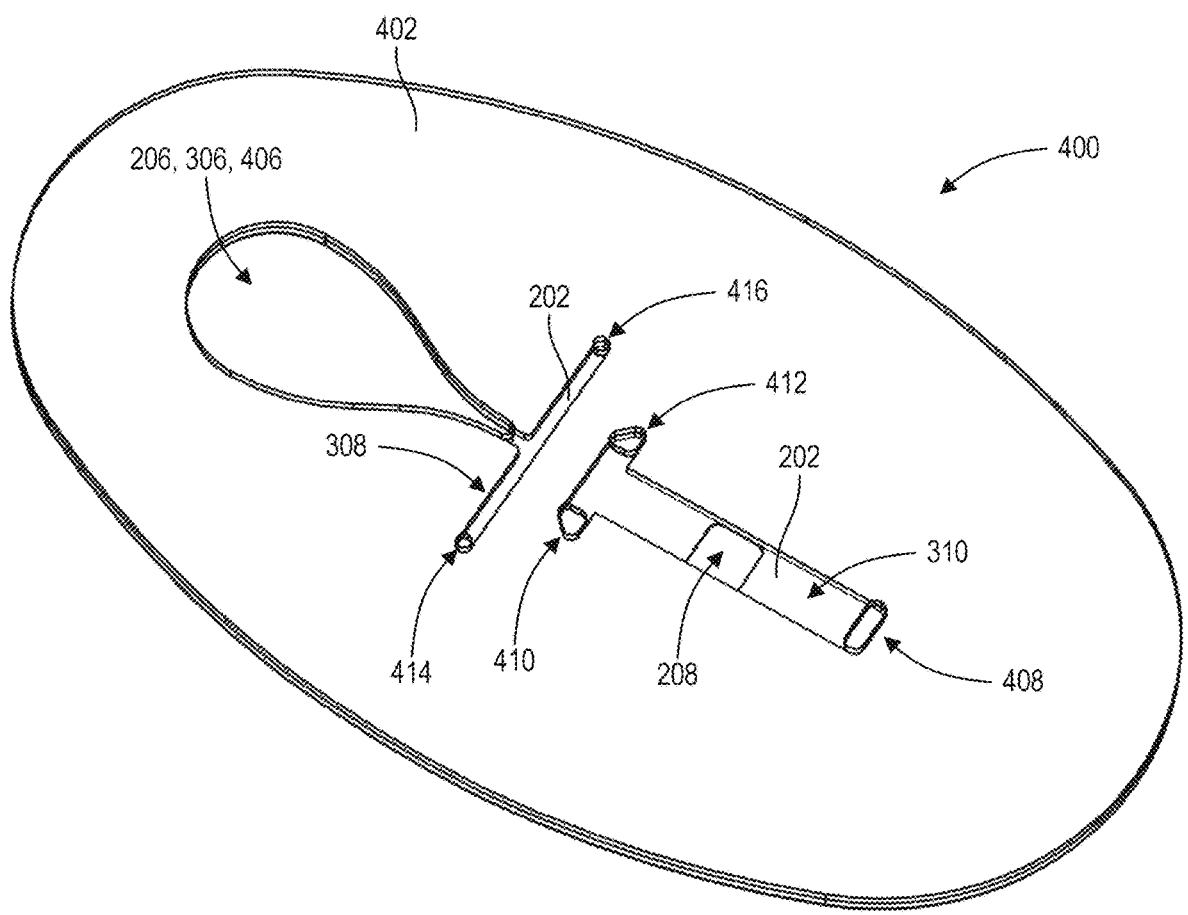
FIG. 14 depicts the adhesive layer, the bottom layer, and the middle layer of the cartridge in accordance with an exemplary embodiment of the present disclosure.

As depicted in FIG. 14, when the cartridge 12 is assembled, the top surface 302 of the bottom layer 300 is attached to the bottom surface 404 of the middle layer 400 such that the sample well opening 306 of the bottom layer 300 and the sample well opening 406 of the middle layer 400 align. Together, the sample well opening 306 and the sample well opening 406 form a sample well of the cartridge 12. In some embodiments, the sample well is configured to retain about 60 µl to about 100 µl. Furthermore, when the bottom layer 300 is attached to the middle layer 400, the middle layer covers a majority of the sample channel 308 and the vacuum channel 310. The vacuum aperture 408 aligns with an end of the shaped vacuum channel 310 and the first vacuum via 410 and the second vacuum via 412 align with opposing sides of an end of vacuum channel 310 such that the vacuum aperture 408, the vacuum via 410 and the second vacuum via 412 provide passage through the middle layer 400 to the vacuum channel 310. That is, the vacuum aperture 408, the vacuum via 410 and the second vacuum via 412 are in open communication with the vacuum channel 310. The first sample via 414 and the second sample via 416 align with opposing ends of the sample channel 308 such that first sample via 414 and the second sample via 416 provide passageway through the middle layer 400 to the sample channel 308. That is, the first sample via 414 and the second sample via 416 are in open communication with the sample channel 308. The sample channel 308 and the first sample via 414 form a first sample pathway and the sample channel 308 and the second sample via 416 form a second sample pathway.

Figure 15:
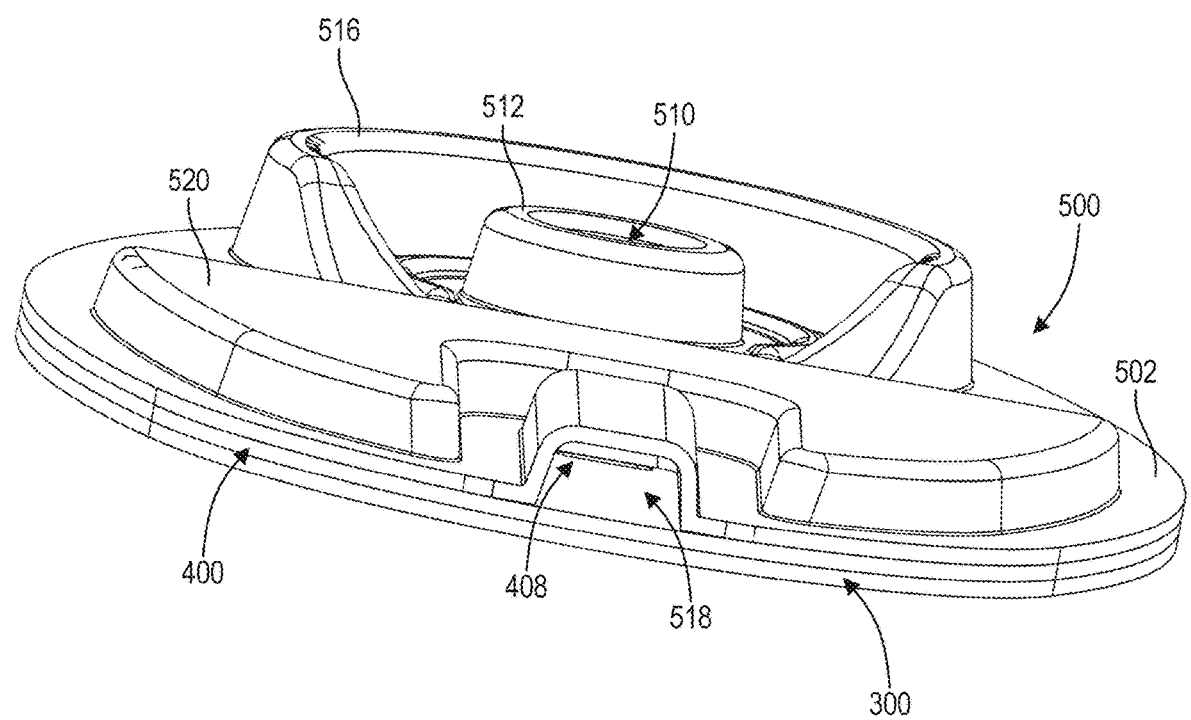
FIG. 15 depicts the bottom layer, the middle layer, and the top layer of the cartridge in accordance with an exemplary embodiment of the present disclosure.
Figure 16:
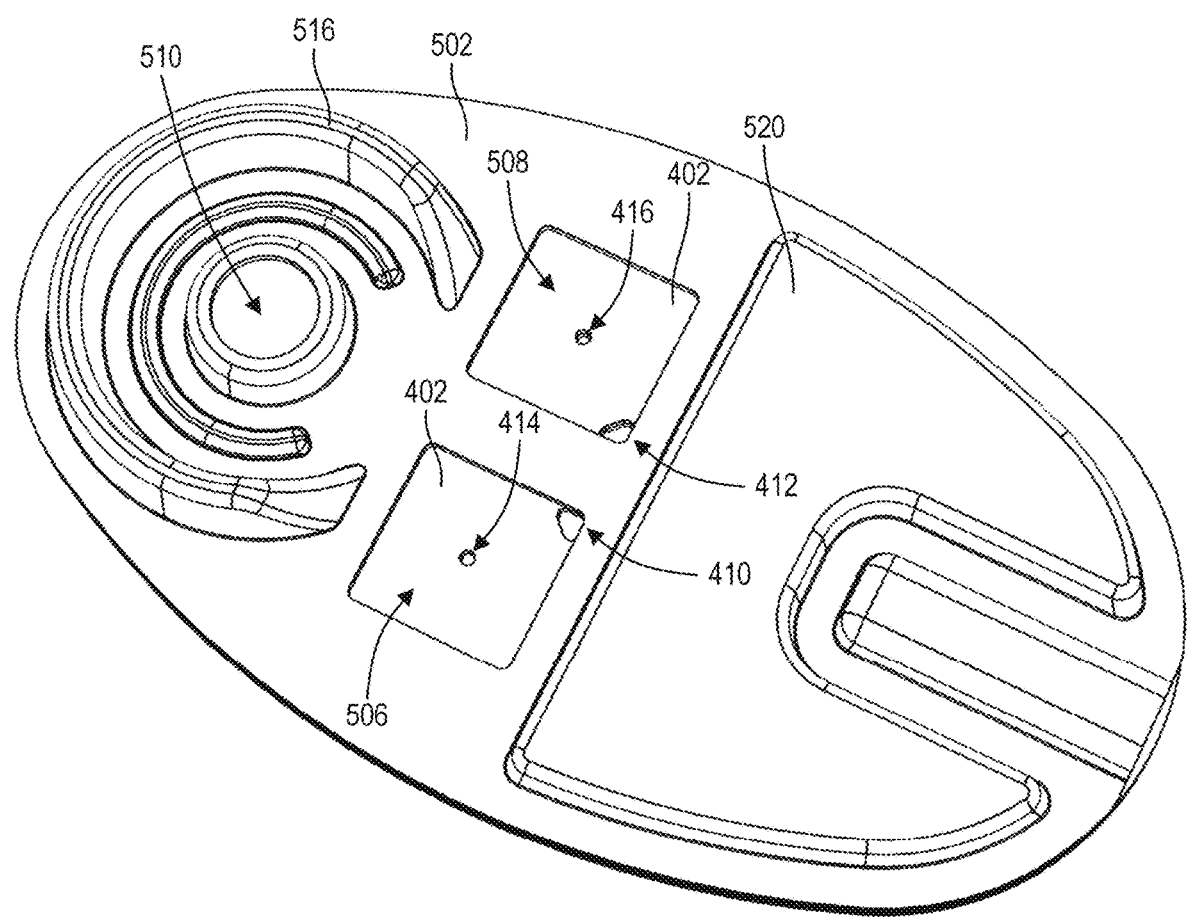
FIG. 16 depicts the top layer and the middle layer of the cartridge in accordance with an exemplary embodiment of the present disclosure.

With reference to FIGS. 15 and 16, when the cartridge 12 is assembled, the top surface 402 of the middle layer 400 is attached to the bottom surface 504 of the top layer 500 such that the needle aperture 510 aligns with the sample well opening 406. That is, the needle aperture 510 aligns with the sample well to provide a passageway through the cartridge 12. Also, when assembled, the first vacuum via 410 aligns with a corner of the first sample collection pad opening 506 and the second vacuum via 412 aligns with a corner of the second sample collection pad opening 508. Furthermore, the first sample via 414 aligns with a center of the first sample collection pad opening 506 and the second sample via 416 aligns with a center of the second sample collection pad opening 508. The first sample collection pad opening 506 provides passageway through the top layer 500 to the first vacuum via 410 and the first sample via 414. That is, the first sample collection pad opening 506 is in open communication with the first vacuum via 410 and the first sample via 414. The second sample collection pad opening 508 provides a passageway through the top layer 500 to the second vacuum via 412 and the second sample via 416. That is, the second sample collection pad opening 508 is in open communication with the second vacuum via 412 and the second sample via 416. When assembled, the groove 518 of the top layer 500 is disposed vertically above the vacuum aperture 408 such the groove 518 is in open communication with the vacuum aperture 408. The top surface 402 of the middle layer 400 and the groove 518 of the top layer 500 define a recess (also referred to herein as a "vacuum pin receptacle") that is shaped and dimensioned to accept at least a portion of the vacuum pin 600. Furthermore, the raised surface 520 and the top surface 402 define a cavity. In some embodiments, the cavity may be about 800 mm$^3$ and may retain about 1 g (e.g., 0.5 g-1.5 g) of desiccant (e.g., Silica Gel).

When the cartridge 12 is assembled, the vacuum aperture 408 is in open communication with the first vacuum via 410 and the second vacuum via 412 via the vacuum channel 310. The vacuum channel 310, the vacuum aperture 408, and the first vacuum via 410 form a first vacuum pathway and the vacuum channel 310, the vacuum aperture 408, and the vacuum channel 310, the vacuum aperture 408, and the second vacuum via 412 form a second vacuum pathway. Furthermore, the first vacuum pathway is in communication with the first sample pathway via the first sample collection pad opening 506 and the second vacuum pathway is in communication with the second sample pathway via the second sample collection pad opening 508.

The bottom layer 300, the middle layer 400, and the top layer 500 may be affixed to one another by ultrasonic welding, laser welding, or pressure sensitive adhesive. In some embodiments, bottom layer 300, the middle layer 400, and the top layer 500 may be formed by die cutting, injection molding, vacuum forming, or pressure molding.

In some embodiments, the bottom layer 300, the middle layer 400, and the top layer 500 may be formed via die cutting or vacuum forming (or other methods) that result in a large reel or sheet of each layer. These reels may be fed into an indexing machine that presses the layers together for coupling the layers together (e.g., by ultrasonic welding, laser welding, pressure sensitive adhesive, heat bonding, heat sealing, heat-activated bonding, or a combination thereof) thereby assembling the cartridge 12.

Figure 17:
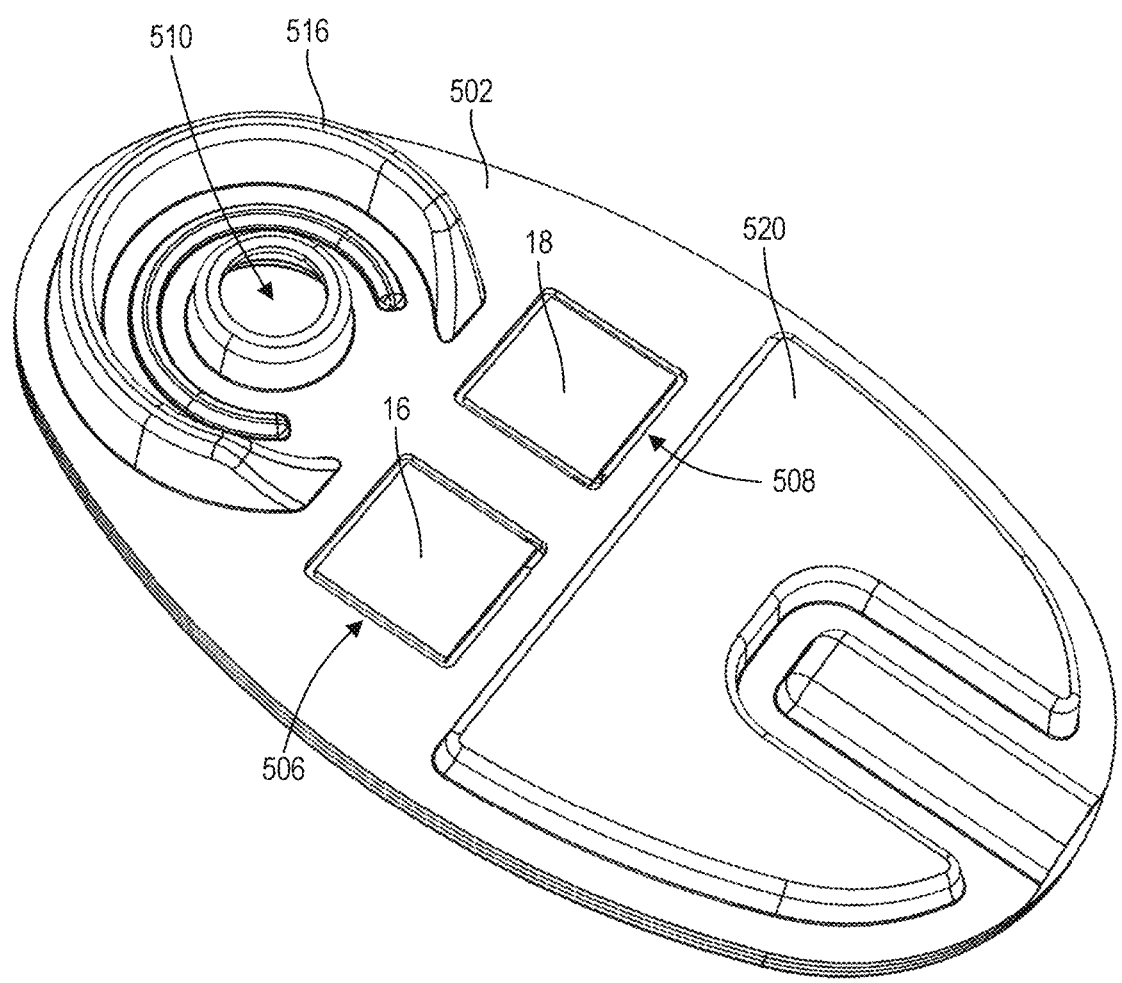
FIG. 17 depicts the cartridge of the dermal patch system with sample collection pads in accordance with an exemplary embodiment of the present disclosure.
Figure 18:
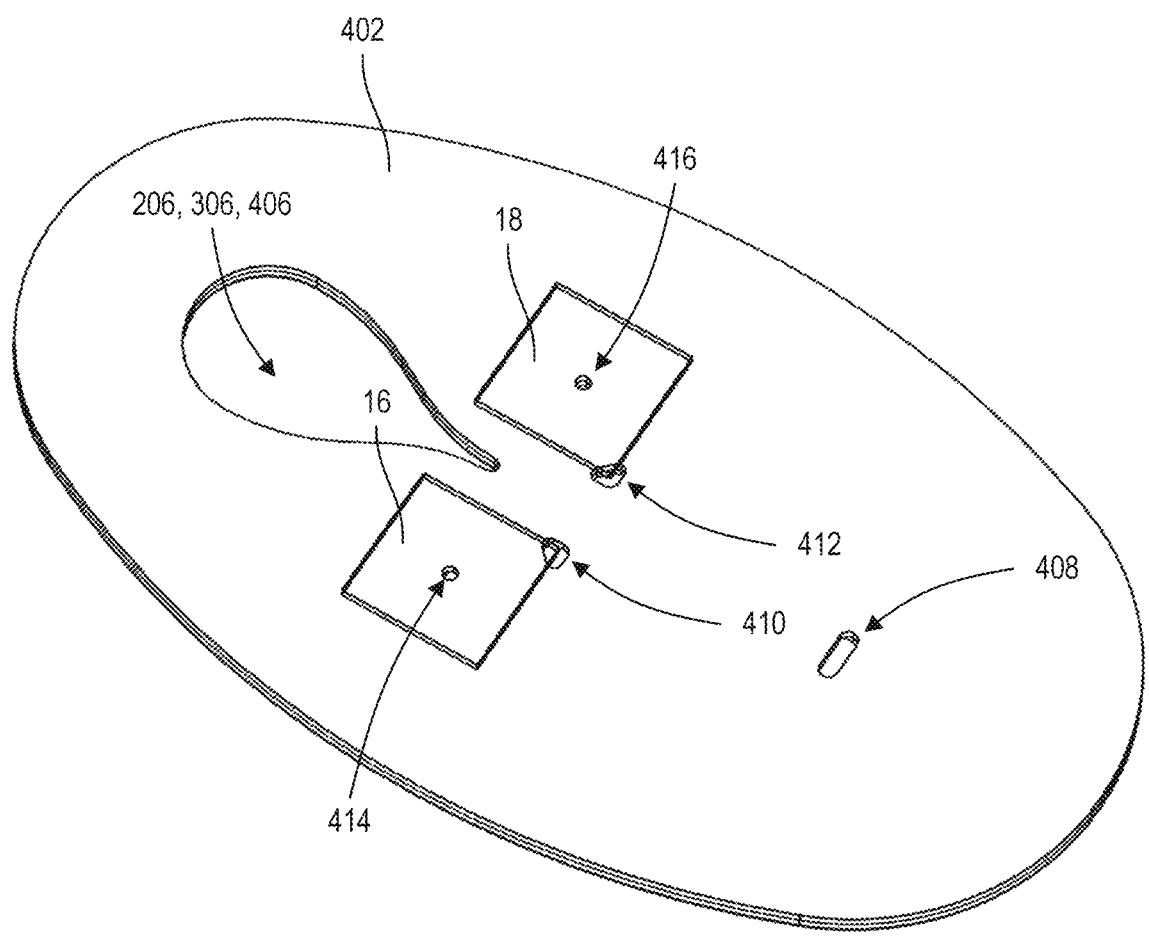
FIG. 18 depicts the middle layer and the sample collection pads in accordance with an exemplary embodiment of the present disclosure.
Figure 19:
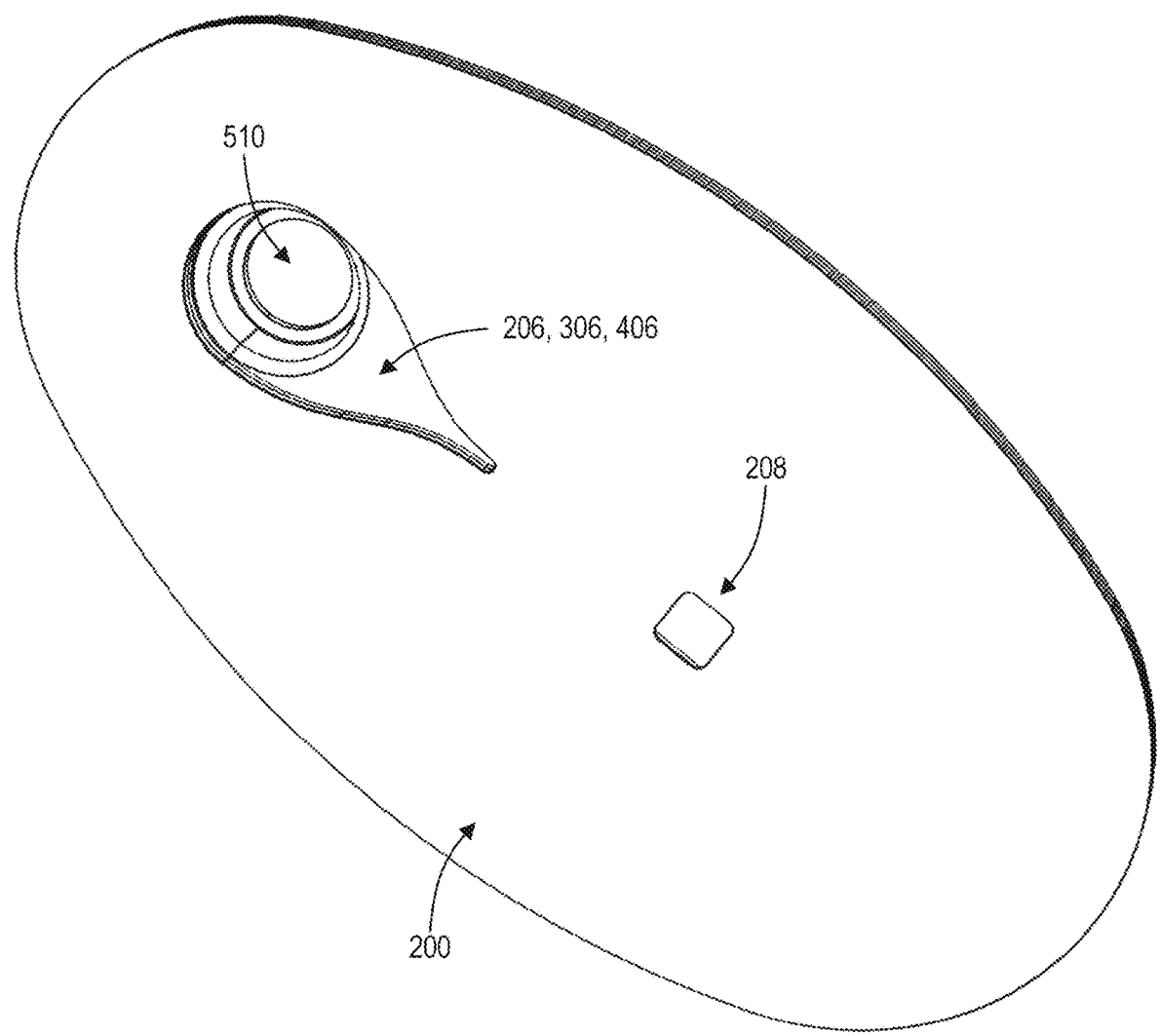
FIG. 19 depicts the bottom of the cartridge of the dermal patch system in accordance with an exemplary embodiment of the present disclosure.

The cartridge 12 further includes a first sample collection pad 16 and a second sample collection pad 18. The first sample collection pad opening 506 is shaped and dimensioned to accommodate the first sample collection pad 16 and the second sample collection pad opening 508 is shaped and dimensioned to accommodate the second sample collection pad 18. As depicted in FIGS. 17 and 18, the first sample collection pad 16 is positioned vertically above, but does not completely cover, the first vacuum via 410 and is positioned vertically above the first sample via 414. Similarly, the second sample collection pad 18 is positioned vertically above, but does not completely cover, the second vacuum via 412 and is positioned vertically above the second sample via 416. In some embodiments, the specimen collection pads 16 and 18 may be a CF12 collection pad or cellulose paper. A CF12 collection pad includes a dried blood spot filter paper that can be used as a specimen collection pad. Other types of collection pads may also be employed in various aspects of the present teachings. In other embodiments, the collection pads can be in direct contact with each other.

The cartridge 12 also includes a clear adhesive seal 20 that covers the first sample collection pad 16 and the second sample collection pad 18 and allows a user to view the first sample collection pad 16 and the second sample collection pad 18. The seal 20 is affixed to the top surface 502 of the top layer 500 such that the seal 20 seals the first sample collection pad 16 and the second sample collection pad 18 between the seal 20 and the middle layer 400. The seal 20 includes a pull tab which allows a user to peel the seal 20 off of the top layer 500 along with the first sample collection pad 16 and the second sample collection pad 18. The cartridge 12 further includes a foil layer 22 that is affixed to the top of the seal 20. The foil layer 22 includes two openings that create a viewing aperture for the first and second sample collection pads 16 and 18 respectively.

Figure 20:
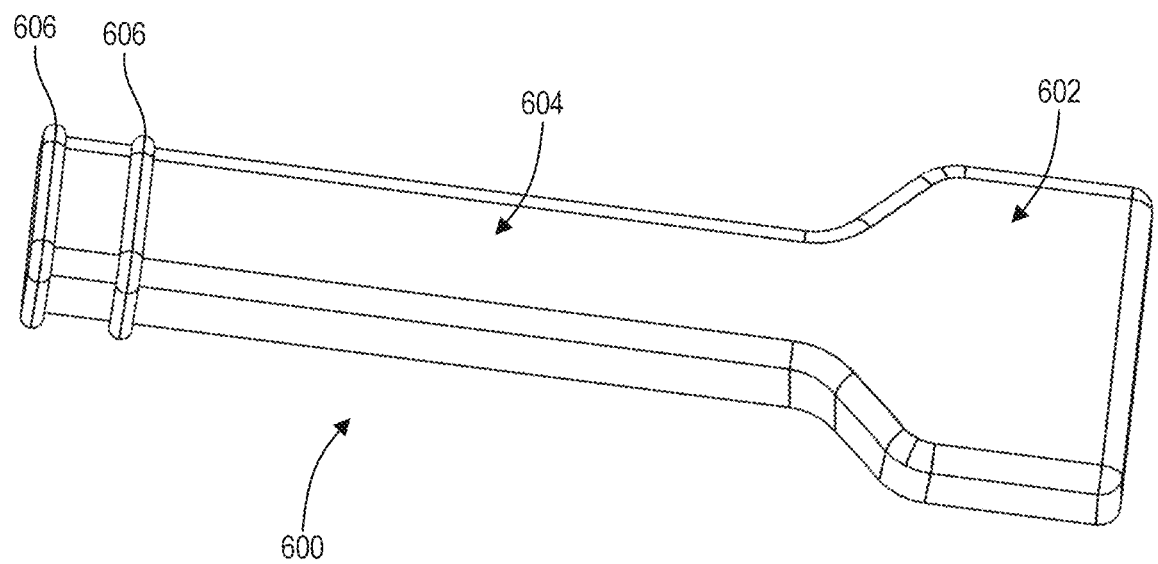
FIG. 20 depicts a vacuum pin of the cartridge in accordance with an exemplary embodiment of the present disclosure.

Referring now to FIG. 20, the vacuum pin 600 is shown in accordance with an exemplary embodiment. In this embodiment, the vacuum pin 600 includes a handle 602 and a neck 604 that extends from the handle 602. The vacuum pin 600 also includes a plurality of ridges 606 that extend vertically from the neck 604. In some embodiments, the ridges 606 may be formed of an elastomeric material. When the vacuum pin 600 is disposed within the vacuum pin receptacle the ridges 606 contact a surface of the vacuum pin receptacle (e.g., a surface of the groove 518) thereby providing an airtight seal between the vacuum pin 600 and the vacuum pin receptacle.

Figure 21:
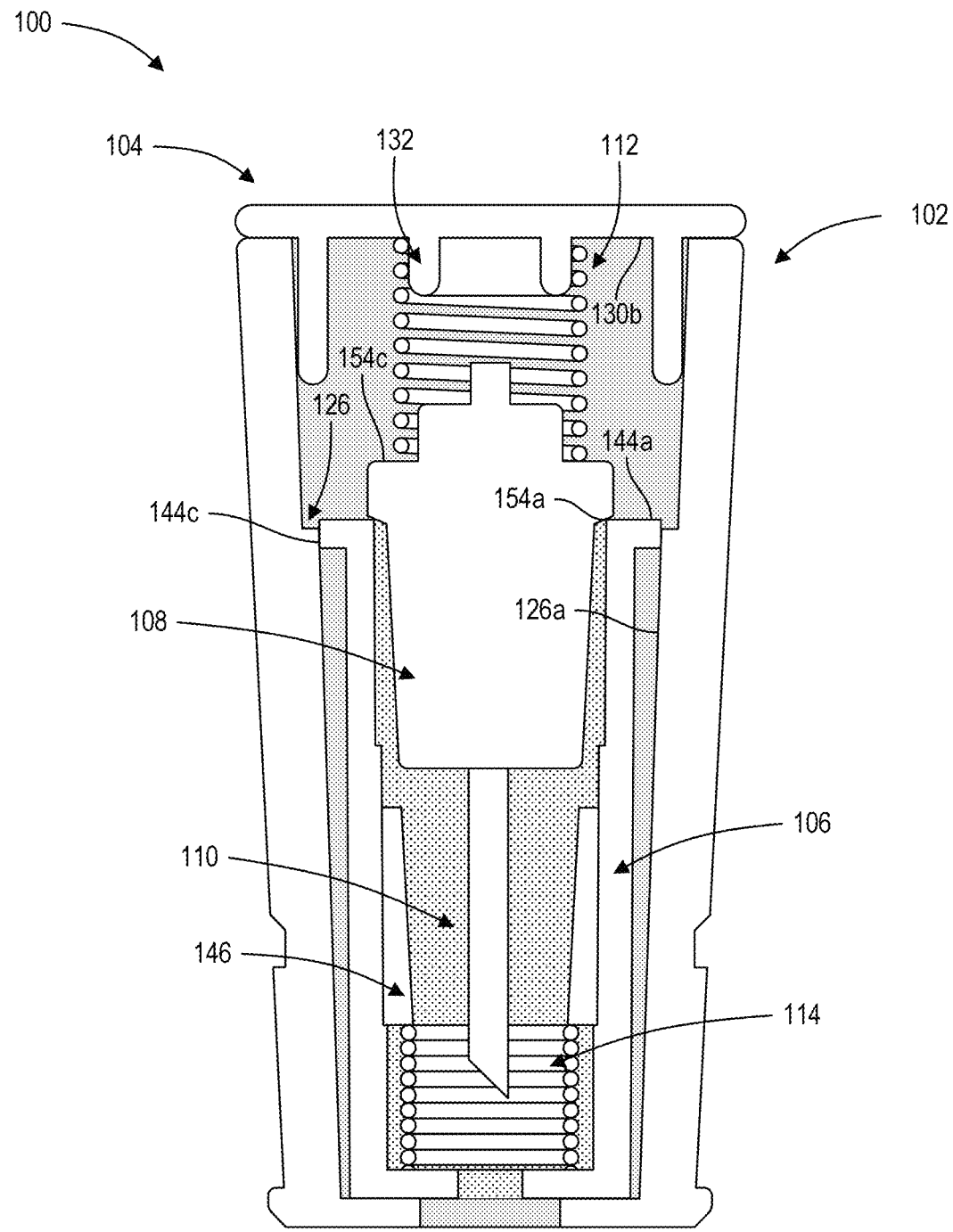
FIG. 21 depicts the lancet of the dermal patch system in an undeployed position in accordance with an exemplary embodiment of the present disclosure.
Figure 22:
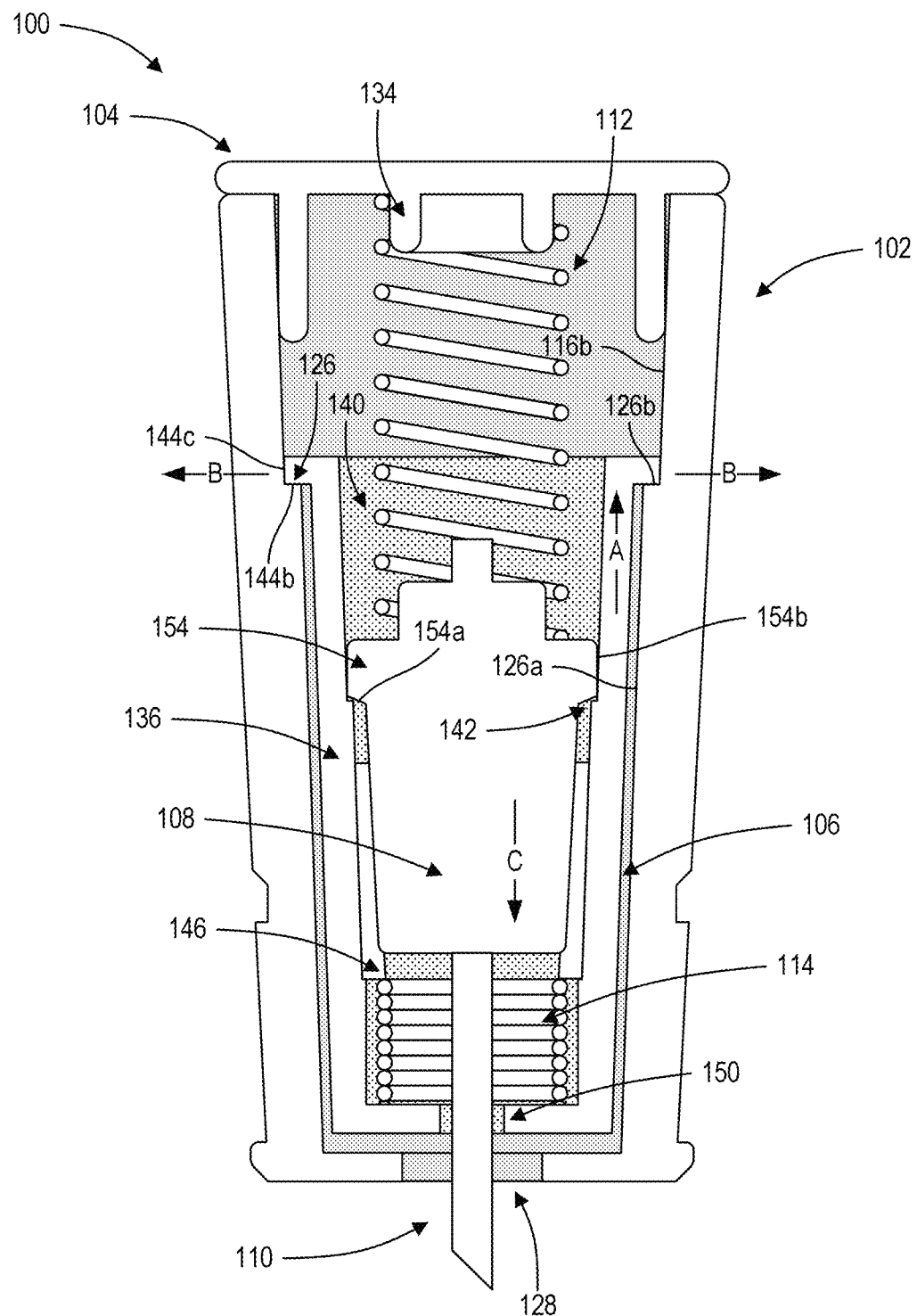
FIG. 22 depicts the lancet of the dermal patch system in a deployed position in accordance with an exemplary embodiment of the present disclosure.
Figure 23:
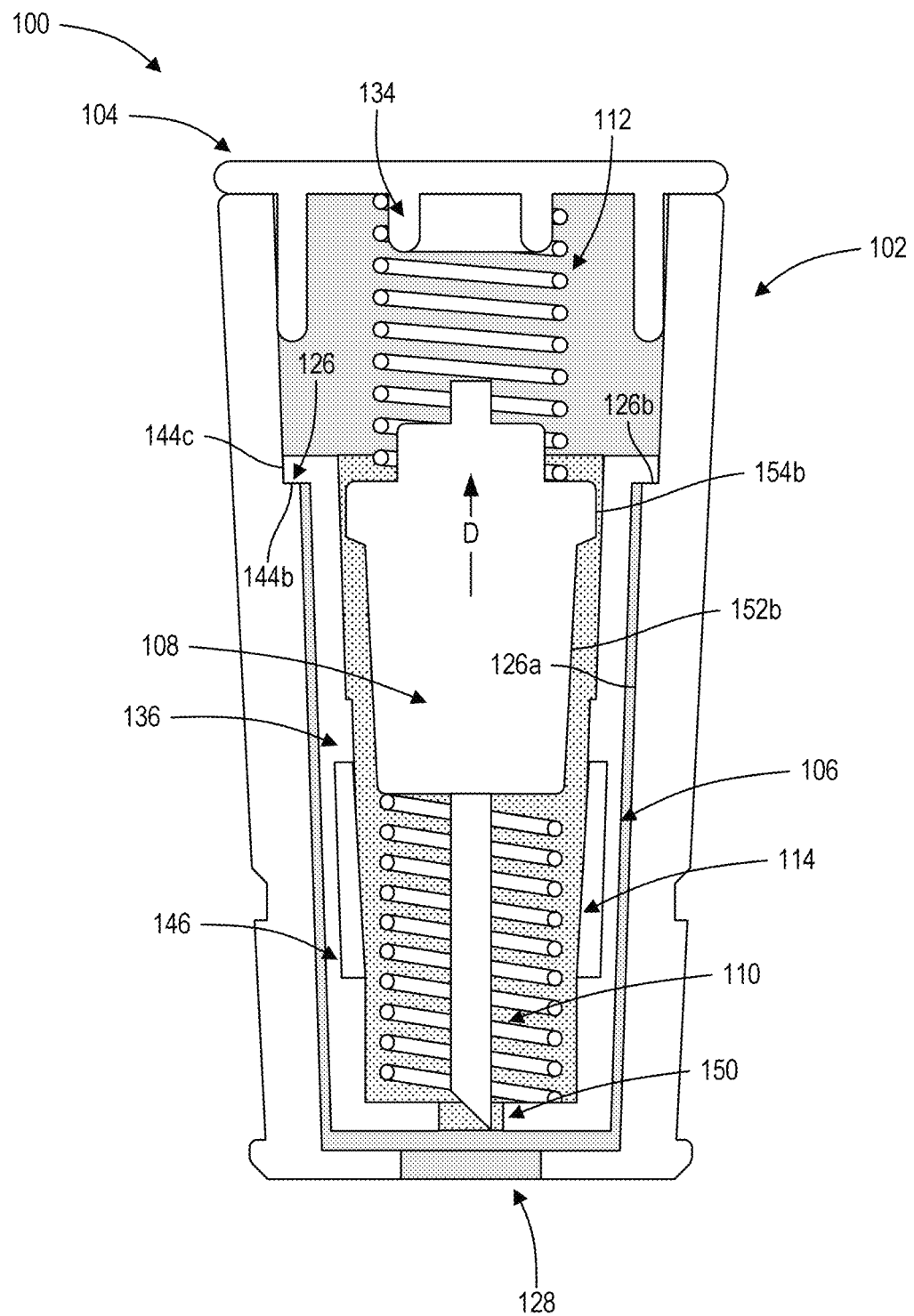
FIG. 23 depicts the lancet of the dermal patch system in a retracted position in accordance with an exemplary embodiment of the present disclosure.

As depicted in FIGS. 21-23, the lancet 100 is moveable between a first position (also referred to as an "undeployed position") (FIG. 21), a second position (also referred to as a "deployed position") (FIG. 22), and a third position (also referred to as a "retracted position") (FIG. 23).

In the undeployed position (before the lancet 100 is pushed into the cartridge 12; FIG. 21) the injection spring 112 and the retraction spring 114 are in a compressed state. In the compressed state, the retraction spring 114 extends vertically between the bottom wall 138 and a proximal end of the locking members 146. More specifically, a distal end of the retraction spring 114 contacts a lower surface of the proximal end of the locking members 146 and a proximal end of the retraction spring 114 contacts the inner surface 138b of the bottom wall 138.

When in the undeployed position the outer surface 144c contacts the inner surface 126a of the columns 126 which compresses the side wall 136 inwardly. Furthermore, the bottom surface 154a of the second cylinder 154 contacts and rests upon the top surfaces 144a of the ledges 144 such that the ledges 144 supports the needle frame 108 in the undeployed position. In this position, the injection spring 112 is prevented from decompressing (due to the second cylinder 154 resting upon the ledges 144) and the needle(s) 110 is disposed completely within the inner volume 140 of the inner sleeve 106.

When the lancet 100 is inserted into the cartridge 12, the engagement of the lancet with the cartridge 12 causes the lancet 100 to automatically move from the undeployed position to the deployed position.

Figure 24:
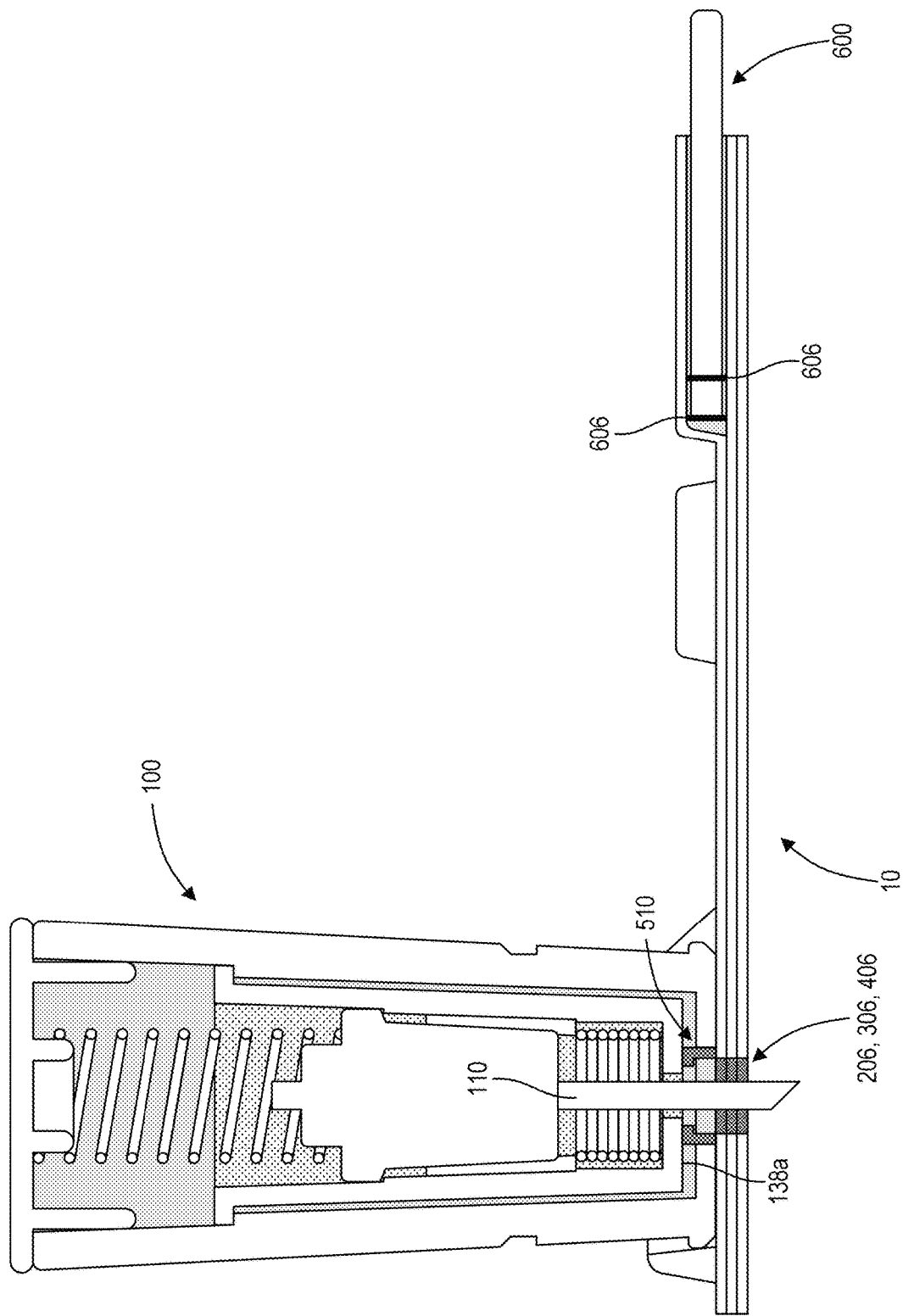
FIG. 24 depicts the lancet pushed into the cartridge, wherein the lancet is in a deployed position in accordance with an exemplary embodiment of the present disclosure.
Figure 25:
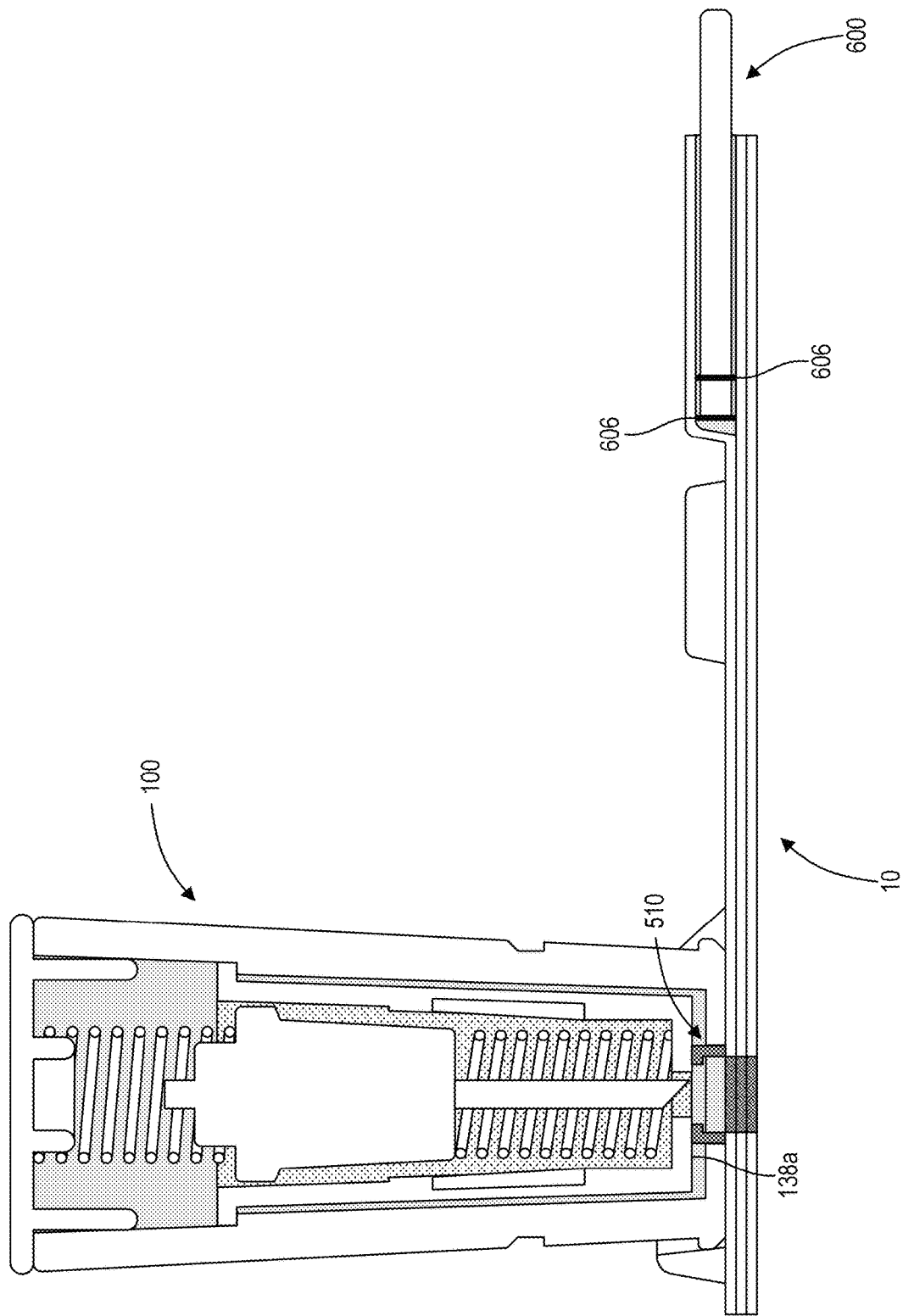
FIG. 25 depicts the lancet pushed into the cartridge, wherein the lancet is in a refracted position in accordance with an exemplary embodiment of the present disclosure.
Figure 26:
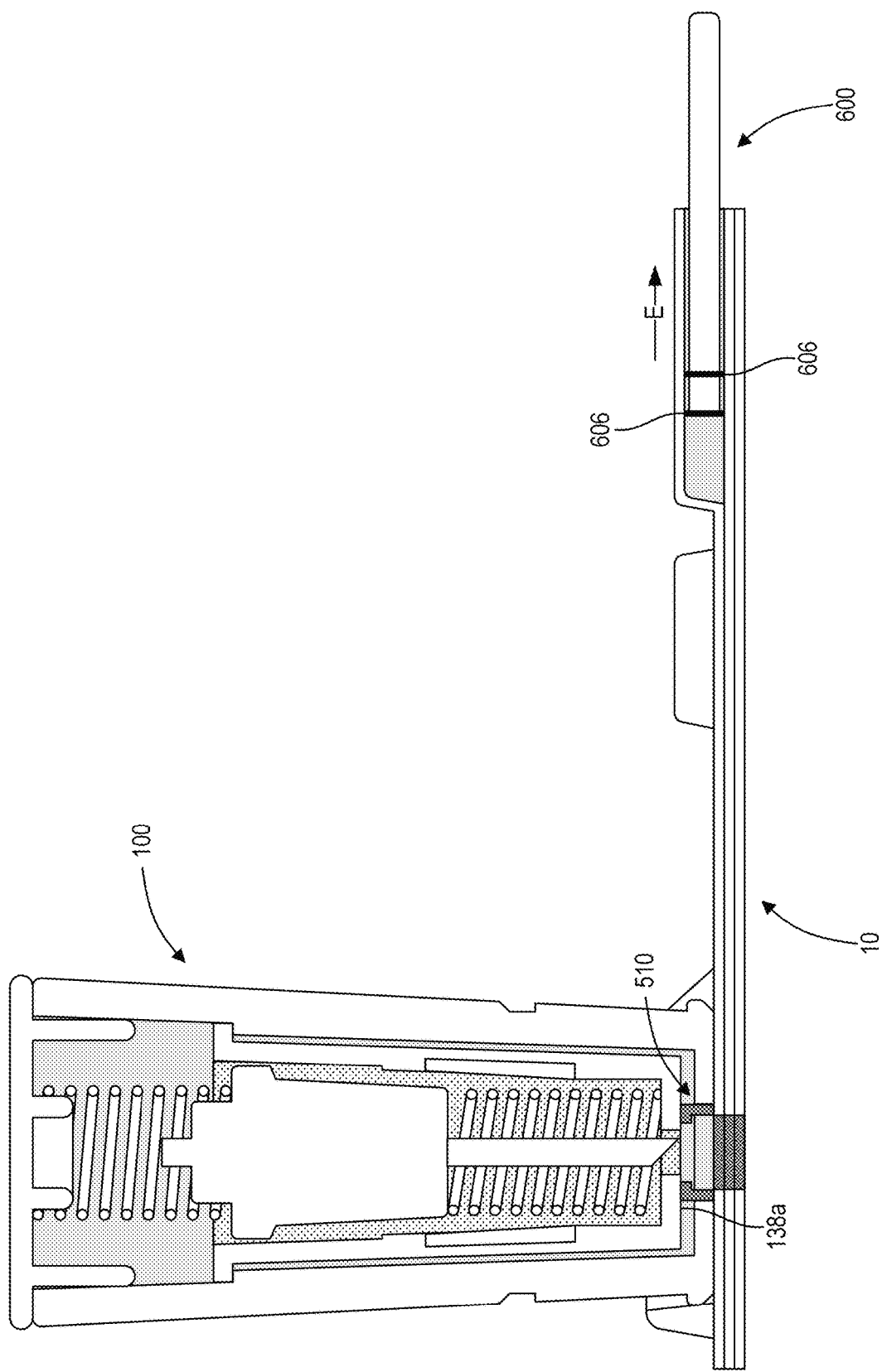
FIG. 26 depicts the lancet pushed into the cartridge, wherein the lancet is in a refracted position and a vacuum pin is in a deployed position in accordance with an exemplary embodiment of the present disclosure.

When the lancet 100 is pushed into the cartridge 12 (FIGS. 24-26), the circular extension 512 extends through the aperture 128 to contact the bottom wall 138. Specifically, a top surface of the circular extension 512 contacts the outer surface 138a of the bottom wall 138 which forces the inner sleeve 106 to move vertically upward in the direction of arrow A (FIG. 22) within the housing 102. This vertical movement causes the ledges 144 to extend vertically above the top surfaces 126b of the columns 126. Moving beyond the top surfaces 126b of the columns 126 allows the side wall 136 to decompress and expand in the direction of arrow B (FIG. 22) and extend toward the inner surface 116b of the side wall 116. In this position, the bottom surface 144b of the ledges 144 rest upon the top surfaces 126b of the columns 126 and the outer surfaces 144c of the ledges 144 contacts the inner surface 116b of the side wall 116.

The expansion of the side wall 136 causes the inner volume 140 of the inner sleeve 106 to have a larger width relative to when the inner sleeve 106 is in the undeployed position such that at least a portion of the side wall 136 has a larger width than the second cylinder 154 (the widest portion of the needle frame 108 which allows the needle frame 108 move vertically downward in the direction of arrow C) (FIG. 22).

Furthermore, the injection spring 112 also causes the needle frame 108 to move in the direction of arrow C as the ledges 144 no longer prevent the injection spring 112 from expanding. The force applied by the injection spring 112 causes the needle frame 108 (and therefore the needle(s) 110) to travel with a force that is sufficient to cause the needle(s) 110 to puncture the skin of a subject wearing the cartridge 12. Stated another way, the injection spring 112 causes the needle(s) 110 to extend through the aperture 150 of the inner sleeve 106, through the aperture 128 of the housing 102, and through the needle aperture 510 and the sample well of the cartridge 12 to puncture the skin of a subject. In the deployed position, the bottom surface 154a of the second cylinder 154 rests upon the columns 142 and at least a portion of the outer surface 154b of the second cylinder 154 contacts the inner surface 136b of the side wall 136.

Figure 12:
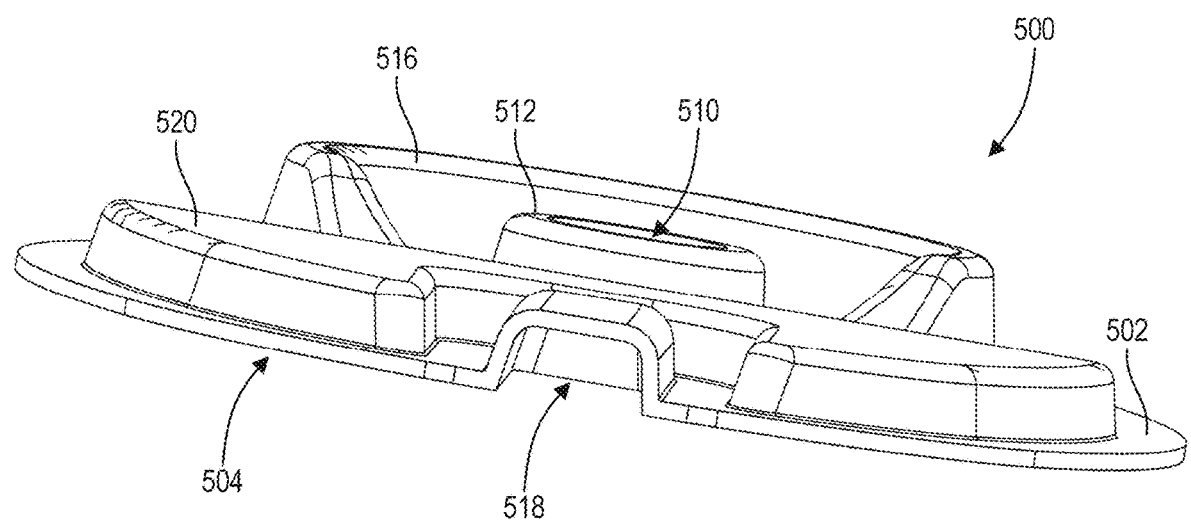

While moving in the direction of arrow C, the outer surface 152b contacts the locking members 146 which causes a proximal portion of locking members 146 that is aligned with an opening 148 to extend into the opening. In this position, the locking members 146 no longer contact the retraction spring 114 thereby allowing the retraction spring 114 to decompress and expand. When decompressed, the retraction spring 114 contacts the outer surface 152b of the first cylinder 152 which causes needle frame 108 to also move in the direction of arrow D (FIG. 12). That is, after moving to the deployed position, the retraction spring 114 causes the needle(s) 110 to retract back into the inner volume 140 of the inner sleeve 106 via the apertures 128 and 150 of the lancet 100. After penetrating the skin of a subject, the retraction spring 114 causes the needle(s) 110 to automatically retract back into the housing of the lancet 100 thereby placing the lancet 100 in the retraced position.

As previously discussed herein, the lancet includes a mechanism that can transition the lancet between a locked state and a released state. In various embodiments, this mechanism includes the columns 126, the ledges 144, and the locking members 146. An upper locking portion of the mechanism refers to the columns 126 and the ledges 144 while a lower locking portion refers to the locking members 146 as the columns 126 and the ledges 144 can be positioned vertically above the locking members 146. The term upper interference portion refers to the top surface 144a of the ledges 144 as this surface interferes with the needle frame's 108 ability to transition to the deployed position when the mechanism is in the locked state. As used herein, a lower interference member refers to the columns 142 as the columns 142 interfere with the needle frame's 108 ability to further extend beyond a desired position.

In use, after affixing the cartridge 12 to the skin of the subject, a user of the dermal patch system 10 pushes the lancet into the cartridge 12 which causes the needle(s) 110 to move to the deployed position and puncture the subject's skin and draw a physiological sample. After the needle(s) 110 retracts into the lancet 100, the drawn physiological sample pools within the physiological sample well of the cartridge 12.

When the physiological sample is within the physiological sample well, a user can pull the vacuum pin 600 in the direction of arrow E (FIG. 26) to move the vacuum pin 600 from a first position (also referred to as an "undeployed" position) (FIGS. 24 and 25) to a second position (FIG. 26) (also referred to as an "deployed" position). Moving the vacuum pin 600 to the deployed position creates a vacuum within the first vacuum pathway, the second vacuum pathway, the second sample pathway, and the second vacuum pathway. The strength of the vacuum is proportional to the amount the vacuum pin 600 moves. That is, the more the vacuum pin 600 moves, the stronger the vacuum. This vacuum causes the drawn physiological sample to travel to the first collection pad 16 and the second collection pad 18 via the first and second sample pathway respectively (FIGS. 17 and 18). In some embodiments, capillary flow, wicking and gravity assist the vacuum pin 600 in drawing the physiological sample towards the collection pads 16 and 18. The first collection pad 16 and the second collection pad 18 absorb the drawn physiological sample. The user can determine the collection pads 16 and 18 have absorbed the physiological sample by viewing the collection pads 16 and 18 through the transparent adhesive seal 20.

After the collection pads 16 and 18 have absorbed the physiological sample, the user can remove the cartridge 12 from the subject's skin. The user can then send the cartridge 12 to a laboratory where a medical professional can remove the collection pads 16 and 18 by pulling the pull tab of the seal 20. Once removed, the medical professional can apply various solutions to the collection pads 16 and 18 which mixes with the physiological sample to form a processed physiological sample that has been freed from the collection pads 16 and 18.

Figure 27:
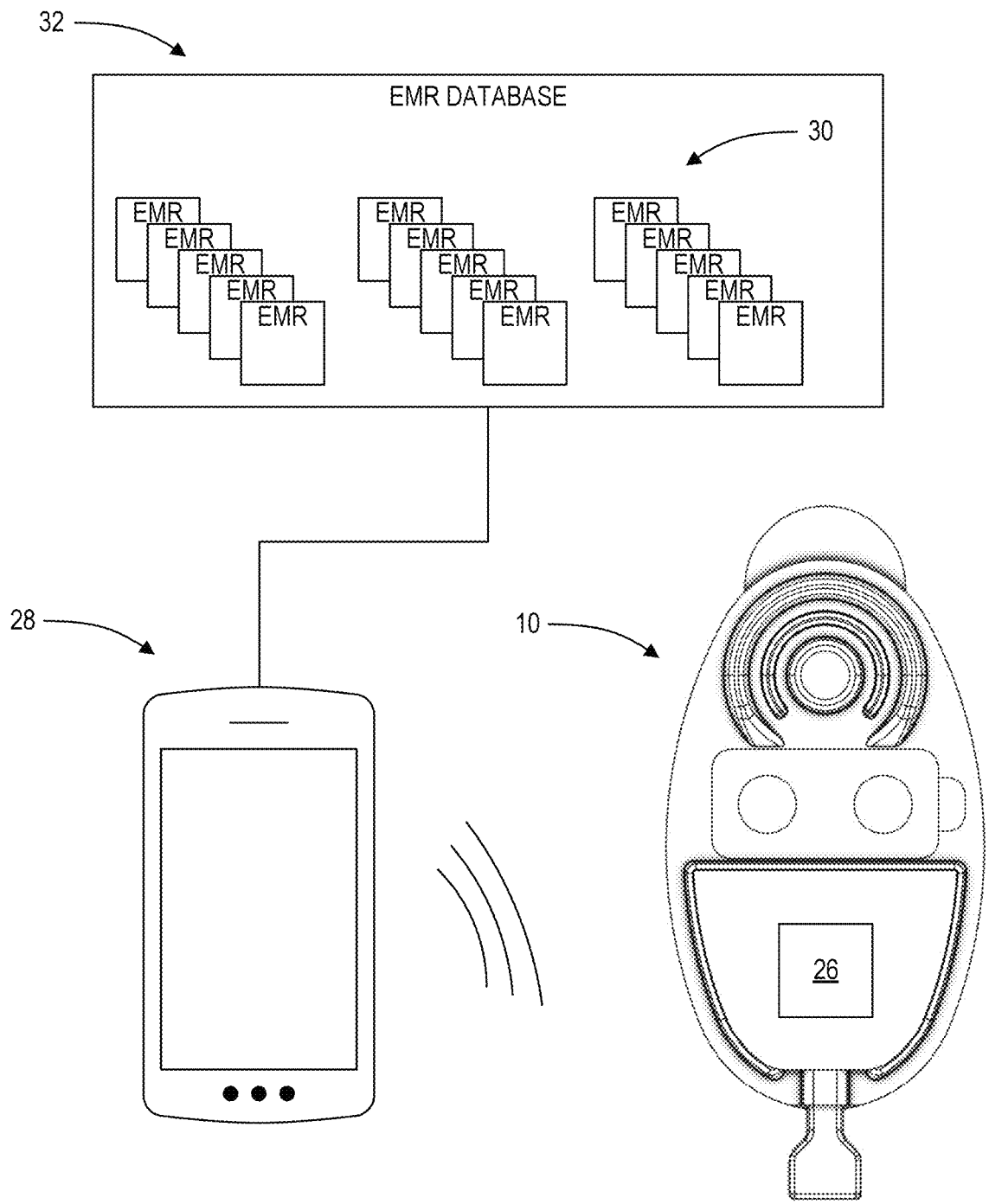
FIG. 27 diagrammatically depicts an electronic medical record database, a computer system, and a cartridge with a quick response ("QR") code in accordance with an exemplary embodiment of the present disclosure.

With reference to FIG. 27, in some embodiments wherein the cartridge 12 includes the QR code 26, a user of a computer system 28 may scan the QR code 26 to determine a test to perform on the stored physiological sample and/or to view and/or update an EMR 30 that is associated with the QR code 26. In these embodiments, the EMR 30 is stored in an EMR database 32 that is in communication with the computer system 28. Furthermore, the QR code 26 may be employed to preserve the chain of custody of the dermal patch system 10.

In these embodiments, the computer system 28 may include an application that provides access to the EMR database 32 via a network connection and allows a user to photograph of scan the QR code 26. As shown in FIG. 27, the EMR database 32 includes a plurality of EMRs 30 each of which is associated with an individual subject. The application causes the computer system 28 to scan or retrieve an image of the QR code 26, analyze the QR code 26 and associate the QR code 26 with an EMR 30. In some embodiments, the computer system 28 may then update the associated EMR 30 to indicate a physiological sample has been obtained from the subject. The computer system 28 may automatically update the EMR 30 automatically or based on a user input. In some embodiments, after associating an EMR 30 with the QR code 26, the computer system 28 may analyze information within the EMR 30 to determine a test to be performed on the obtained physiological sample and may prompt a user of the computer system to perform the test.

Figure 28:
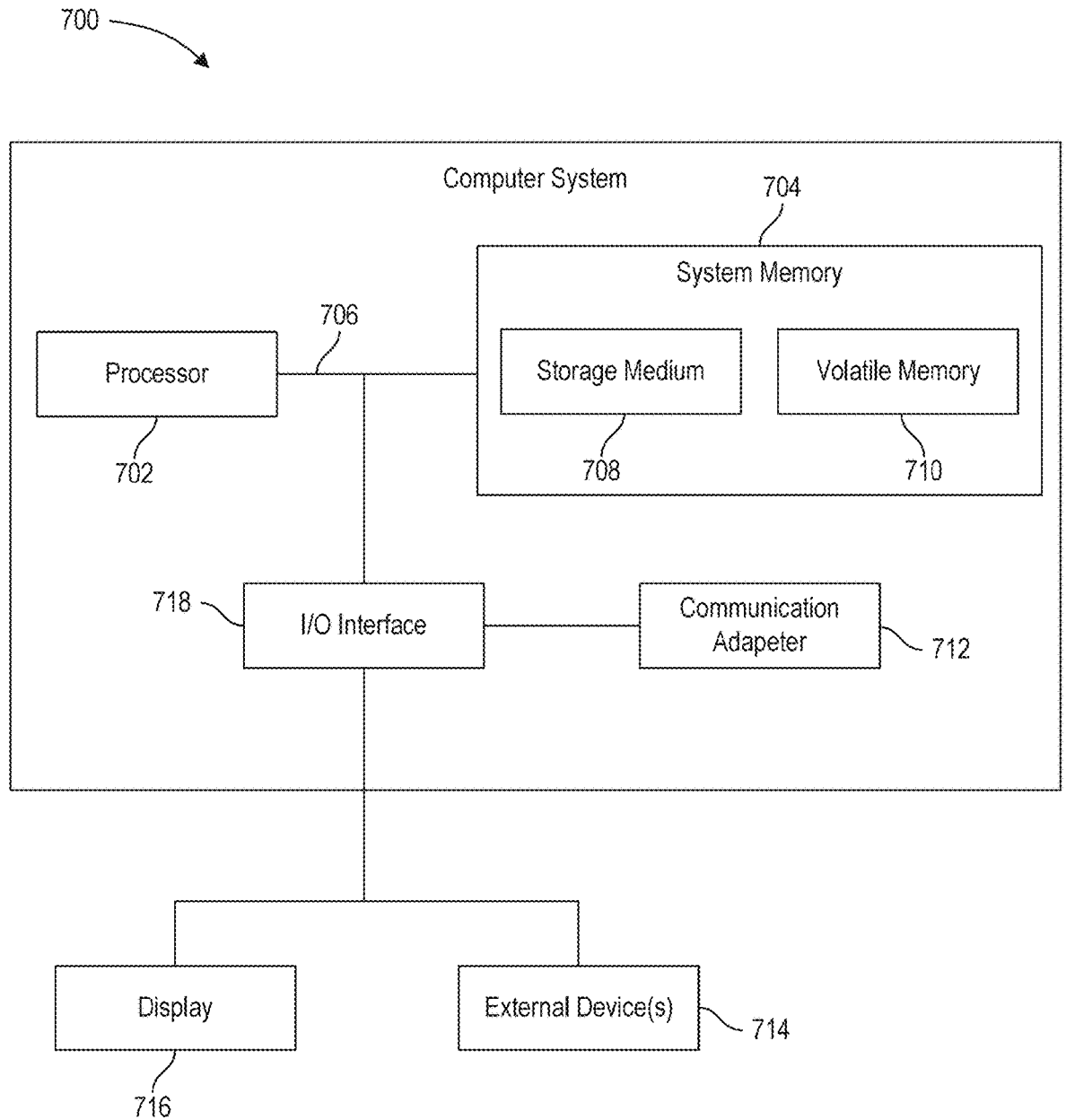
FIG. 28 diagrammatically depicts a computer system in accordance with an exemplary embodiment of the present disclosure.

Referring now to FIG. 28, a computer system 700 is shown in accordance with an exemplary embodiment. The computer system 700 may serve as any computer system disclosed herein (e.g., the computer system 28). As used herein a computer system (or device) is any system/device capable of receiving, processing, and/or sending data. Computer systems include, but are not limited to, microprocessor-based systems, personal computers, servers, hand-held computing devices, tablets, smartphones, multiprocessor-based systems, mainframe computer systems, virtual reality ("VR") headsets and the like.

As shown in FIG. 28, the computer system 700 includes one or more processors or processing units 702, a system memory 704, and a bus 706 that couples the various components of the computer system 700 including the system memory 704 to the processor 702. The system memory 704 includes a computer readable storage medium 708 and volatile memory 710 (e.g., Random Access Memory, cache, etc.). As used herein, a computer readable storage medium includes any media that is capable of storing computer readable; program instructions and is accessible by a processor. The computer readable storage medium 708 includes non-volatile and non-transitory storage media (e.g., flash memory, read only memory (ROM), hard disk drives, etc.). Computer program instructions as described herein include program modules (e.g., routines, programs, objects, components, logic, data structures, etc.) that are executable by a processor. Furthermore, computer readable program instructions, when executed by a processor, can direct a computer system to function in a particular manner such that a computer readable storage medium comprises an article of manufacture. Specifically, the computer readable program instructions when executed by a processor can create a means for carrying out at least a portion of the steps of the methods disclosed herein.

The bus 706 may be one or more of any type of bus structure capable of transmitting data between components of the computer system 700 (e.g., a memory bus, a memory controller, a peripheral bus, an accelerated graphics port, etc.).

The computer system 700 may further include a communication adapter 712 which allows the computer system 700 to communicate with one or more other computer systems/devices via one or more communication protocols (e.g., Wi-Fi, BTLE, etc.) and in some embodiments may allow the computer system 700 to communicate with one or more other computer systems/devices over one or more networks (e.g., a local area network (LAN), a wide area network (WAN), a public network (the Internet), etc.).

In some embodiments, the computer system 700 may be connected to one or more external devices 714 and a display 716. As used herein, an external device includes any device that allows a user to interact with a computer system (e.g., mouse, keyboard, touch screen, etc.). An external device 714 and the display 716 may be in communication with the processor 702 and the system memory 704 via an Input/Output (I/O) interface 718.

The display 716 may display a graphical user interface (GUI) that may include a plurality of selectable icons and/or editable fields. A user may use an external device 714 (e.g., a mouse) to select one or more icons and/or edit one or more editable fields. Selecting an icon and/or editing a field may cause the processor 702 to execute computer readable program instructions stored in the computer readable storage medium 708. In one example, a user may use an external device 714 to interact with the computer system 700 and cause the processor 702 to execute computer readable program instructions relating to at least a portion of the steps of the methods disclosed herein.

Figure 29:
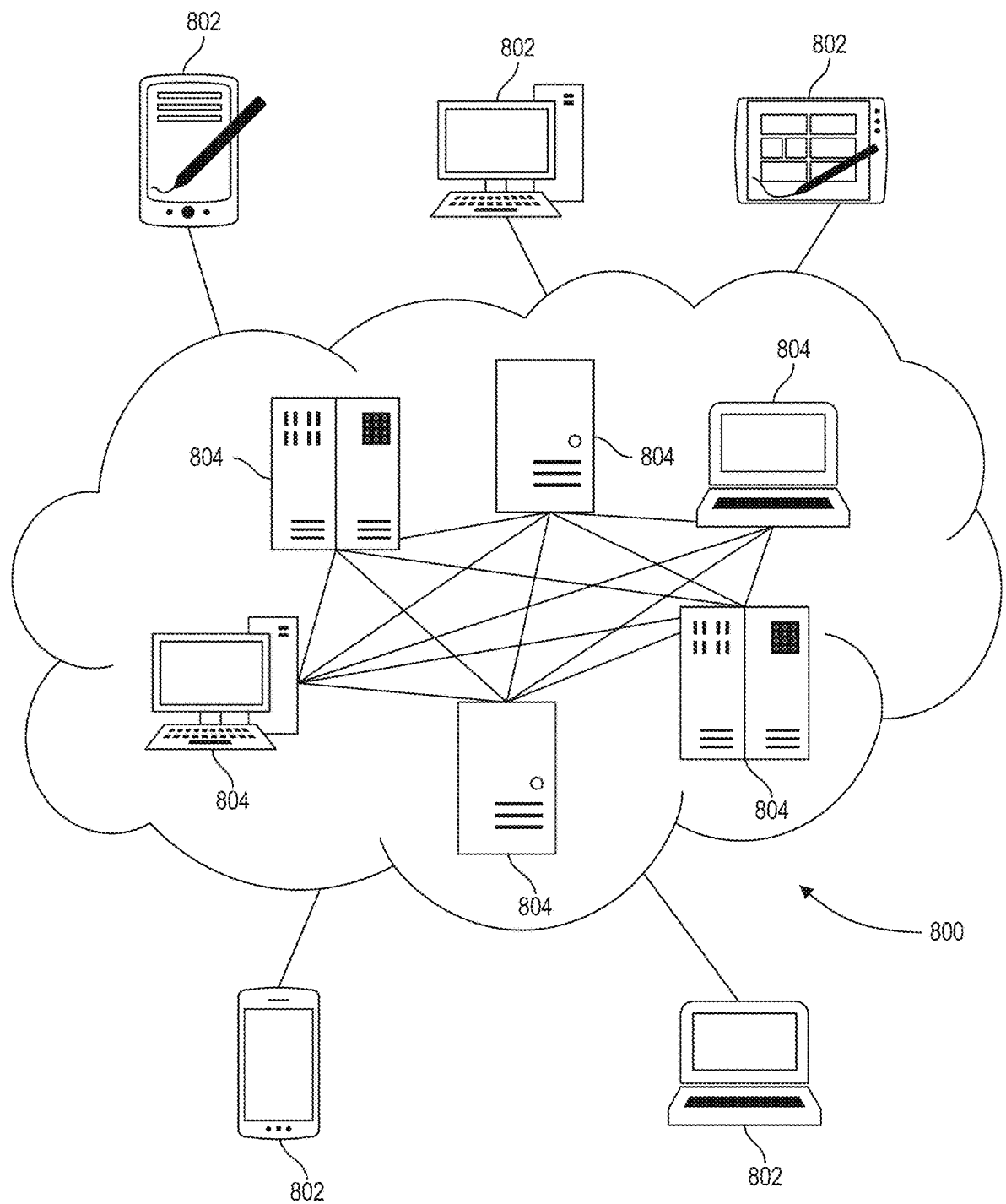
FIG. 29 diagrammatically depicts a cloud computing environment in accordance with an exemplary embodiment of the present disclosure.

Referring now to FIG. 29, a cloud computing environment 800 is depicted in accordance with an exemplary embodiment. The cloud computing environment 800 is connected to one or more user computer systems 802 and provides access to shared computer resources (e.g., storage, memory, applications, virtual machines, etc.) to the user computer systems 802. As depicted in FIG. 29, the cloud computing environment includes one or more interconnected nodes 804. Each node 804 may be a computer system or device local processing and storage capabilities. The nodes 804 may be grouped and in communication with one another via one or more networks. This allows the cloud computing environment 800 to offer software services to the one or more computer services to the one or more user computer systems 802 and as such, a user computer system 802 does not need to maintain resources locally.

In one embodiment, a node 804 includes computer readable program instructions for carrying out various steps of various methods disclosed herein. In these embodiments, a user of a user computer system 802 that is connected to the cloud computing environment may cause a node 804 to execute the computer readable program instructions to carry out various steps of various methods disclosed herein.

Figure 30:
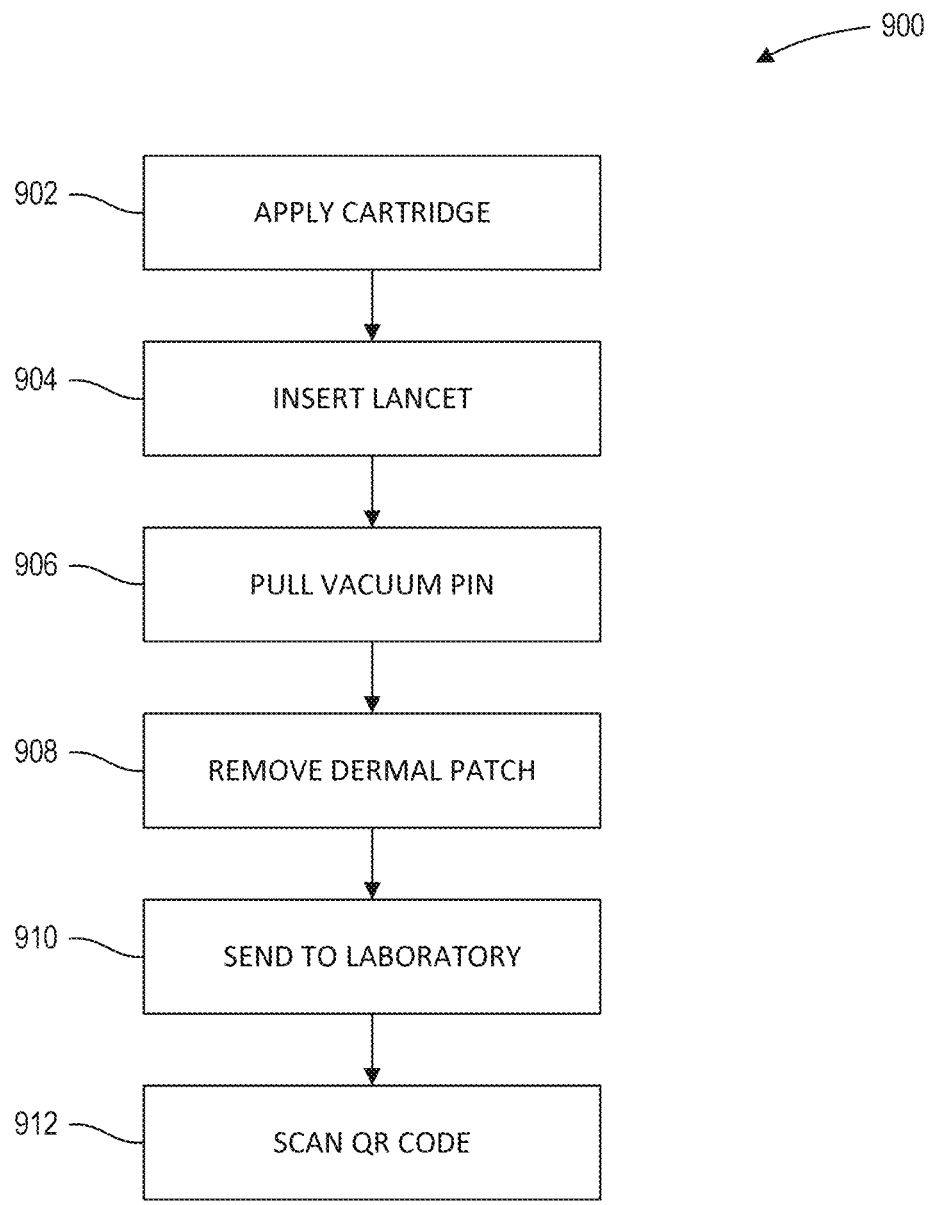
FIG. 30 is a flow chart of a method for running a diagnostic test on a drawn physiological sample in accordance with an exemplary embodiment of the present disclosure.

Referring now to FIG. 30, a method for obtaining a physiological sample from a subject is shown in accordance with an exemplary embodiment.

At 902 a user (e.g., a medical professional, a subject, etc.) removes the protective liner 14 from the cartridge 12 to expose the adhesive layer 200 and applies the cartridge 12 to the skin of the subject via the adhesive layer 200 at a suitable location (e.g., on a leg, arm, etc.) as previously discussed herein.

At 904, the user pushes the lancet 100 into the cartridge 12 to draw a physiological sample (e.g., a blood sample, a sample of interstitial fluid, etc.) from the subject as previously discussed herein.

At 906, the user pulls the vacuum pin 600 to draw the physiological sample to the specimen collection pads 16 and 18 as previously discussed herein.

At 908, the user removes the cartridge 12 from the skin of the subject as previously discussed herein.

At 910, the user sends the specimen collection pads 16 and 18 to a laboratory for further analysis by a medical professional. In some embodiments, the user first removes the specimen collection pads 16 and 18 from the cartridge 12 by pulling the pull tab of the seal 20. In other embodiments, the user sends the cartridge 12 with the specimen collection pads 16 and 18 to the medical professional. In these embodiments, the cartridge 12 may include a desiccant which dries the specimen collection pads 16 and 18.

At 912, a user of the computer system 28 scans the QR code 26 and updates an EMR 30 to indicate a physiological sample was collected from the subject as previously discussed herein.

As previously discussed, some of the steps of the various methods disclosed herein may be implemented by way of computer readable instructions, encoded or embedded on computer readable storage medium (which excludes transitory medium), which, when executed by a processor(s), cause the processor(s) to carry out various steps of the methods of the present disclosure.

While various embodiments have been illustrated and described in detail in the drawings and foregoing description, such illustration and description are to be considered illustrative or exemplary and not restrictive; embodiments of the present disclosure are not limited to the disclosed embodiments. Other variations to the disclosed embodiments can be understood and effected by those skilled in the art in practicing embodiments of the present disclosure, from a study of the drawings, the disclosure, and the appended claims.

In the claims, the word "comprising" does not exclude other elements or steps, and the indefinite article "a" or "an" does not exclude a plurality. A single processor or other processing unit may fulfill the functions of several items recited in the claims. The mere fact that certain measures are recited in mutually different dependent claims does not indicate that a combination of these measured cannot be used to advantage. Any reference signs in the claims should not be construed as limiting the scope.

What is claimed is:

1. A dermal patch system for collecting a physiological sample comprising:
a cartridge, wherein the cartridge includes:
a bottom material layer that is configured to attach to the subject's skin,
a top material layer, and
a middle material layer disposed between and coupled to the bottom material layer and the top material layer,
wherein the top material layer and the middle material layer cooperatively define a vacuum pin receptacle, and
a sample collection pad,
a vacuum pin disposed within the vacuum pin receptacle, wherein the vacuum pin is moveable within the vacuum pin receptacle between an undeployed position and a deployed position to create a vacuum within the cartridge,
a lancet including at least one needle, wherein the lancet is configured to automatically move the at least one needle from an undeployed position to a deployed position when the lancet is engaged into the cartridge,
wherein the at least one needle is configured to draw a physiological sample from the subject when the at least one needle is in the deployed position and the cartridge is attached to the subject's skin,
wherein the vacuum facilitates the transfer of the physiological sample to the sample collection pad.

2. The dermal patch system of claim 1, wherein the lancet is separate from the cartridge.

3. The dermal patch system of claim 1, wherein the lancet is configured to automatically retract the at least one needle into the lancet from the deployed position.

4. The dermal patch system of claim 1, wherein the cartridge includes a desiccant.

5. The dermal patch system of claim 1, wherein the bottom material layer and the middle material layer define a sample well configured to retain the drawn physiological sample.

6. The dermal patch system of claim 5, wherein the sample well is configured to retain about 60 µl to about 100 µl of physiological fluid.

7. The dermal patch system of claim 5, wherein the top material layer includes a needle aperture and the at least one needle extends through the needle aperture and the sample well to draw the physiological sample.

8. The dermal patch system of claim 5, wherein the cartridge further includes:
a sample pathway in open communication with the sample well and the sample collection pad,
wherein the sample pathway is configured to carry the physiological sample from the sample well to the sample collection pad.

9. The dermal patch system of claim 8, wherein the sample collection pad rests upon the top surface of the middle material layer.

10. The dermal patch system of claim 9, wherein the sample collection pad is disposed vertically above the sample pathway.

11. The dermal patch system of claim 9, wherein the sample pathway extends through the bottom material layer and the middle material layer.

12. The dermal patch system of claim 8, wherein the cartridge further includes:
a vacuum pathway in open communication with the sample collection pad,
wherein moving the vacuum pin to the deployed position creates the vacuum within the vacuum pathway and the sample pathway.

13. The dermal patch system of claim 12, wherein the vacuum pathway extends through the bottom material layer and the middle material layer.

14. The dermal patch system of claim 1, wherein the sample collection pad is a CF12 collection pad.

15. The dermal patch system of claim 1, wherein the cartridge further includes:
a quick response code disposed on the top material layer, wherein the quick response code is associated with an electronic medical record.

16. The dermal patch system of claim 1, wherein the cartridge further includes: an adhesive seal that covers the sample collection pad and seals the cartridge.

17. The dermal patch system of claim 1, wherein the sample collection pad is a first sample collection pad and the cartridge includes a second sample collection pad and the vacuum draws the physiological sample to the first sample collection pad and the second sample collection pad.

18. The dermal patch system of claim 1, wherein the strength of the vacuum is proportional to the amount the vacuum pin moves.

* * * * *